(12) United States Patent
Derelöv

(10) Patent No.: US 12,320,374 B2
(45) Date of Patent: *Jun. 3, 2025

(54) SYMMETRIC TONGUE AND T-CROSS

(71) Applicant: Välinge Innovation AB, Viken (SE)

(72) Inventor: Peter Derelöv, Helsingborg (SE)

(73) Assignee: VÄLINGE INNOVATION AB, Viken (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/441,480

(22) Filed: Feb. 14, 2024

(65) Prior Publication Data

US 2024/0360860 A1 Oct. 31, 2024

Related U.S. Application Data

(63) Continuation of application No. 18/058,037, filed on Nov. 22, 2022, now Pat. No. 11,933,335, which is a
(Continued)

(30) Foreign Application Priority Data

Apr. 18, 2018 (SE) .................................... 1850441-5

(51) Int. Cl.
*F16B 12/24* (2006.01)
*A47B 47/00* (2006.01)
(Continued)

(52) U.S. Cl.
CPC .......... *F16B 12/24* (2013.01); *A47B 47/0075* (2013.01); *A47B 47/042* (2013.01);
(Continued)

(58) Field of Classification Search
CPC .... E04C 2/38; E04C 2/40; F16B 12/24; F16B 12/125; F16B 12/26; A47B 47/0075;
(Continued)

(56) References Cited

U.S. PATENT DOCUMENTS 291,032 A 1/1884 Cleland
634,581 A 10/1899 Miller
(Continued)

FOREIGN PATENT DOCUMENTS

AT 400611 B 2/1996
AU 2016254803 A1 10/2017
(Continued)

OTHER PUBLICATIONS

Extended European Search Report mailed Dec. 17, 2021 in EP Patent Application No. 19789380.3, European Patent Office, Munich, DE, 7 pages.

(Continued)

*Primary Examiner* — Patrick J Maestri
(74) *Attorney, Agent, or Firm* — Boone IP Law

(57) ABSTRACT

A set including a first panel, a second panel and a mechanical locking device for locking the first panel to the second panel, the mechanical locking device includes an insertion groove at the second edge surface, a flexible tongue positioned in the insertion groove and an edge tongue including a tongue groove, the flexible tongue includes a first locking surface and a second locking surface, the first locking surface is configured to cooperate with the tongue groove for locking of the first panel to the second panel in a first direction when the flexible tongue is positioned in the insertion groove in a first orientation, the second locking surface of the flexible tongue is configured to cooperate with the tongue groove for a locking of the first panel to the second panel in a first direction when the flexible tongue is positioned in the insertion groove in a second orientation.

15 Claims, 13 Drawing Sheets

Related U.S. Application Data continuation of application No. 16/386,874, filed on Apr. 17, 2019, now Pat. No. 11,536,307.

(51) Int. Cl.

| | |
|---|---|
| *A47B 47/04* | (2006.01) |
| *A61M 5/14* | (2006.01) |
| *E04F 15/02* | (2006.01) |
| *E04F 15/04* | (2006.01) |
| *E04F 15/10* | (2006.01) |
| *F16B 12/12* | (2006.01) |
| *F16B 12/26* | (2006.01) |
| *A47B 61/00* | (2006.01) |
| *A47B 63/00* | (2006.01) |
| *A47B 77/00* | (2006.01) |
| *A47B 88/90* | (2017.01) |
| *B65D 6/34* | (2006.01) |

(52) U.S. Cl.
CPC ..... *A61M 5/1413* (2013.01); *E04F 15/02011* (2013.01); *E04F 15/02038* (2013.01); *E04F 15/04* (2013.01); *E04F 15/102* (2013.01); *E04F 15/105* (2013.01); *F16B 12/125* (2013.01); *F16B 12/26* (2013.01); *A47B 61/00* (2013.01); *A47B 63/00* (2013.01); *A47B 77/00* (2013.01); *A47B 88/941* (2017.01); *A47B 2230/0081* (2013.01); *A47B 2230/0096* (2013.01); *B65D 9/34* (2013.01); *E04F 2201/0138* (2013.01); *E04F 2201/0505* (2013.01); *E04F 2201/0535* (2013.01); *E04F 2201/0547* (2013.01); *Y10T 403/7075* (2015.01)

(58) Field of Classification Search
CPC ......... A47B 47/042; A47B 2230/0081; A61M 5/1413; E04F 2201/0505; E04F 2201/0535; E04F 2201/0547

See application file for complete search history.

(56) References Cited

U.S. PATENT DOCUMENTS

| | | |
|---|---|---|
| 701,000 A | 5/1902 | Ahrens. |
| 861,911 A | 7/1907 | Stewart et al. |
| 881,673 A | 3/1908 | Ellison |
| 1,533,099 A | 4/1925 | Carroll |
| 1,534,468 A | 4/1925 | Shea, Jr. |
| 1,800,386 A | 4/1931 | Hoffman |
| 1,800,387 A | 4/1931 | Greist |
| 1,802,245 A | 4/1931 | Foretich |
| 1,954,242 A | 4/1934 | Heppenstall |
| 2,360,451 A | 10/1944 | Stone |
| 2,362,904 A | 11/1944 | Kramer |
| 2,496,184 A | 1/1950 | Von Canon |
| 2,681,483 A | 6/1954 | Morawetz |
| 3,002,630 A | 10/1961 | Heisser |
| 3,195,968 A | 7/1965 | Freeman |
| 3,284,152 A | 11/1966 | Schorghuber |
| 3,313,054 A | 4/1967 | Madey |
| 3,347,610 A | 10/1967 | Pilliod |
| 3,410,441 A | 11/1968 | Rhyne |
| 3,722,704 A | 3/1973 | Piretti |
| 3,722,971 A | 3/1973 | Zeischegg |
| 3,742,807 A | 7/1973 | Manning |
| 3,765,465 A | 10/1973 | Gulistan |
| 3,784,271 A | 1/1974 | Schreiber |
| 3,884,002 A | 5/1975 | Logie |
| 3,885,845 A | 5/1975 | Krieks |
| 3,981,118 A | 9/1976 | Johnson et al. |
| 4,089,614 A | 5/1978 | Harley |
| 4,099,293 A | 7/1978 | Pittasch |
| 4,099,887 A | 7/1978 | Mackenroth |
| 4,116,510 A | 9/1978 | Franco |
| 4,142,271 A | 3/1979 | Busse |
| 4,211,379 A | 7/1980 | Morgan et al. |
| 4,222,544 A | 9/1980 | Crowder |
| 4,279,397 A | 7/1981 | Larsson |
| 4,299,067 A | 11/1981 | Bertschi |
| 4,308,961 A | 1/1982 | Kunce |
| 4,324,517 A | 4/1982 | Dey |
| 4,403,886 A | 9/1983 | Haeusler |
| 4,405,253 A | 9/1983 | Stockum |
| 4,509,648 A | 4/1985 | Govang et al. |
| 4,593,734 A | 6/1986 | Wallace |
| 4,595,105 A | 6/1986 | Gold |
| 4,597,122 A | 7/1986 | Handler et al. |
| 4,615,448 A | 10/1986 | Johnstonbaugh |
| 4,629,076 A | 12/1986 | Amstutz et al. |
| 4,750,794 A | 6/1988 | Vegh |
| 4,752,150 A | 6/1988 | Salice |
| 4,815,908 A | 3/1989 | Duran et al. |
| 4,817,900 A | 4/1989 | Whittington et al. |
| 4,844,266 A | 7/1989 | Small et al. |
| 4,883,331 A | 11/1989 | Mengel |
| 4,886,326 A | 12/1989 | Kuzyk |
| 4,888,933 A | 12/1989 | Guomundsson et al. |
| 4,891,897 A | 1/1990 | Gieske et al. |
| 4,909,581 A | 3/1990 | Haheeb |
| 4,938,625 A | 7/1990 | Matsui |
| 4,944,416 A | 7/1990 | Petersen et al. |
| 4,961,295 A | 10/1990 | Kosch et al. |
| 5,004,116 A | 4/1991 | Cattarozzi |
| 5,018,323 A | 5/1991 | Clausen |
| 5,109,993 A | 5/1992 | Hutchison |
| 5,114,265 A | 5/1992 | Grisley |
| 5,121,578 A | 6/1992 | Holz |
| 5,125,518 A | 6/1992 | Ward |
| 5,138,803 A | 8/1992 | Grossen |
| 5,209,556 A | 5/1993 | Anderson |
| 5,212,925 A | 5/1993 | McClinton |
| 5,299,509 A | 4/1994 | Ballard |
| 5,360,121 A | 11/1994 | Sothman |
| 5,375,802 A | 12/1994 | Branham, II |
| 5,423,155 A | 6/1995 | Bauer |
| 5,451,102 A | 9/1995 | Chuan |
| 5,458,433 A | 10/1995 | Stastny |
| 5,471,804 A | 12/1995 | Winter, IV |
| 5,475,960 A | 12/1995 | Lindal |
| 5,499,667 A | 3/1996 | Nakanishi |
| 5,499,886 A | 3/1996 | Short et al. |
| 5,507,331 A | 4/1996 | Nakanishi |
| 5,527,103 A | 6/1996 | Pittman |
| 5,536,108 A | 7/1996 | Kvalheim |
| 5,658,086 A | 8/1997 | Brokaw et al. |
| 5,711,115 A | 1/1998 | Wirt |
| 5,775,521 A | 7/1998 | Tisbo |
| 5,810,505 A | 9/1998 | Henriott et al. |
| 5,893,617 A | 4/1999 | Lee |
| 5,941,026 A | 8/1999 | Eisenreich et al. |
| 5,944,294 A | 8/1999 | Baer |
| 5,950,389 A | 9/1999 | Porter |
| 6,045,290 A | 4/2000 | Nocievski |
| 6,050,426 A | 4/2000 | Leurdijk |
| 6,142,436 A | 11/2000 | Thurston et al. |
| 6,312,186 B1 | 11/2001 | Roeck et al. |
| 6,349,507 B1 | 2/2002 | Muellerleile |
| 6,363,645 B1 | 4/2002 | Hunter |
| 6,413,007 B1 | 7/2002 | Lambright |
| 6,418,683 B1 | 7/2002 | Martensson et al. |
| 6,491,172 B2 | 12/2002 | Chance et al. |
| 6,505,452 B1 | 1/2003 | Hannig et al. |
| 6,547,086 B1 | 4/2003 | Harvey |
| 6,578,498 B1 | 6/2003 | Draudt et al. |
| 6,675,979 B2 | 1/2004 | Taylor |
| D486,676 S | 2/2004 | Campbell et al. |
| 6,769,219 B2 | 8/2004 | Schwitte et al. |
| 6,772,890 B2 | 8/2004 | Campbell et al. |
| 6,827,028 B1 | 12/2004 | Callaway |
| 6,971,614 B2 | 12/2005 | Fischer et al. |
| 7,127,860 B2 | 10/2006 | Pervan et al. |

(56) References Cited

U.S. PATENT DOCUMENTS

| | | |
|---|---|---|
| 7,223,045 B2 | 5/2007 | Migli |
| 7,228,977 B2 | 6/2007 | Perkins et al. |
| 7,300,120 B2 | 11/2007 | Shin |
| 7,451,535 B2 | 11/2008 | Wells et al. |
| 7,451,578 B2 | 11/2008 | Hannig |
| 7,584,583 B2 | 9/2009 | Bergelin et al. |
| 7,614,350 B2 | 11/2009 | Tuttle et al. |
| 7,621,092 B2 | 11/2009 | Groeke et al. |
| 7,641,414 B1 | 1/2010 | Joyce |
| 7,717,278 B2 | 5/2010 | Kao |
| 7,721,503 B2 | 5/2010 | Pervan et al. |
| 7,793,450 B2 | 9/2010 | Chasmer et al. |
| 7,818,939 B2 | 10/2010 | Bearinger et al. |
| 7,998,549 B2 | 8/2011 | Susnjara |
| 8,033,074 B2 | 10/2011 | Pervan et al. |
| 8,038,363 B2 | 10/2011 | Hannig et al. |
| 8,042,311 B2 | 10/2011 | Pervan et al. |
| 8,146,754 B2 | 4/2012 | Apgood et al. |
| 8,220,217 B2 | 7/2012 | Muehlebach |
| 8,234,830 B2 | 8/2012 | Pervan et al. |
| 8,365,499 B2 | 2/2013 | Nilsson et al. |
| 8,387,327 B2 | 3/2013 | Pervan |
| 8,464,408 B2 | 6/2013 | Hazzard |
| 8,495,849 B2 | 7/2013 | Pervan |
| 8,505,257 B2 | 8/2013 | Boo et al. |
| 8,544,230 B2 | 10/2013 | Pervan |
| 8,596,013 B2 | 12/2013 | Boo |
| 8,602,227 B1 | 12/2013 | McDonald |
| 8,615,952 B2 | 12/2013 | Engstrom |
| 8,713,886 B2 | 5/2014 | Pervan et al. |
| 8,745,952 B2 | 6/2014 | Perra et al. |
| 8,764,137 B2 | 7/2014 | Fehre |
| 8,776,473 B2 | 7/2014 | Pervan et al. |
| 8,833,028 B2 | 9/2014 | Whispell et al. |
| 8,864,407 B1 | 10/2014 | Sorum |
| 8,882,416 B2 | 11/2014 | Baur et al. |
| 8,887,468 B2 | 11/2014 | Hakansson et al. |
| 9,175,703 B2 | 11/2015 | Maertens et al. |
| 9,216,541 B2 | 12/2015 | Boo et al. |
| 9,290,948 B2 | 3/2016 | Cappelle et al. |
| 9,375,085 B2 | 6/2016 | Derelv |
| 9,538,842 B2 | 1/2017 | Hkansson et al. |
| 9,617,741 B2 | 4/2017 | Devos |
| 9,655,442 B2 | 5/2017 | Boo et al. |
| 9,700,157 B2 | 7/2017 | Keyvanloo |
| 9,714,672 B2 | 7/2017 | Derelv |
| 9,723,923 B2 | 8/2017 | Derelv |
| 9,726,210 B2 | 8/2017 | Derelv et al. |
| 9,745,756 B2 | 8/2017 | Hannig |
| 9,758,973 B2 | 9/2017 | Segaert et al. |
| 9,763,528 B2 | 9/2017 | Lung et al. |
| 9,809,983 B2 | 11/2017 | Trudel |
| 9,945,121 B2 | 4/2018 | Derelv |
| 10,034,541 B2 | 7/2018 | Boo et al. |
| 10,202,996 B2 | 2/2019 | Hkansson et al. |
| 10,378,570 B2 | 8/2019 | Broughton |
| 10,415,613 B2 | 9/2019 | Boo |
| 10,448,739 B2 | 10/2019 | Derelov et al. |
| 10,451,097 B2 | 10/2019 | Brnnstrm et al. |
| 10,486,245 B2 | 11/2019 | Fridlund |
| 10,506,875 B2 | 12/2019 | Boo et al. |
| 10,544,818 B2 | 1/2020 | Fridlund |
| 10,548,397 B2 | 2/2020 | Derelv et al. |
| 10,669,716 B2 | 6/2020 | Derelv |
| 10,670,064 B2 | 6/2020 | Derelv |
| 10,724,564 B2 | 7/2020 | Derelv |
| 10,731,688 B2 | 8/2020 | Brnnstrm et al. |
| 10,736,416 B2 | 8/2020 | Derelv et al. |
| 10,830,266 B2 | 11/2020 | Fridlund |
| 10,830,268 B2 | 11/2020 | Boo |
| 10,871,179 B2 | 12/2020 | Hkansson et al. |
| 10,876,562 B2 | 12/2020 | Pervan |
| 10,876,563 B2 | 12/2020 | Derelv et al. |
| 10,968,936 B2 | 4/2021 | Boo et al. |
| 11,076,691 B2 | 8/2021 | Boo |
| 11,083,287 B2 | 8/2021 | Boo et al. |
| 11,098,484 B2 | 8/2021 | Derelov |
| 11,137,007 B2 | 10/2021 | Fridlund |
| 11,204,051 B2 | 12/2021 | Brnnstrm et al. |
| 11,246,415 B2 | 2/2022 | Derelov et al. |
| 11,272,783 B2 | 3/2022 | Derelv |
| 11,326,636 B2 | 5/2022 | Pervan |
| 11,428,253 B2 | 8/2022 | Hakansson et al. |
| 2002/0170258 A1 | 11/2002 | Schwitte et al. |
| 2004/0165946 A1 | 8/2004 | Areh et al. |
| 2005/0042027 A1 | 2/2005 | Migli |
| 2005/0236544 A1 | 10/2005 | Mancino et al. |
| 2005/0247653 A1 | 11/2005 | Brooks |
| 2006/0091093 A1 | 5/2006 | Armari |
| 2006/0101769 A1 | 5/2006 | Pervan et al. |
| 2006/0180561 A1 | 8/2006 | Wisnoski et al. |
| 2006/0236642 A1 | 10/2006 | Pervan |
| 2006/0273085 A1 | 12/2006 | Casto |
| 2007/0006543 A1 | 1/2007 | Engstrom |
| 2007/0028547 A1 | 2/2007 | Grafenauer et al. |
| 2007/0182214 A1 | 8/2007 | Okabe et al. |
| 2007/0193178 A1 | 8/2007 | Groeke et al. |
| 2008/0010937 A1 | 1/2008 | Pervan et al. |
| 2008/0066415 A1 | 3/2008 | Pervan et al. |
| 2008/0134607 A1 | 6/2008 | Pervan et al. |
| 2008/0193209 A1 | 8/2008 | Henderson |
| 2008/0216435 A1 | 9/2008 | Nolan |
| 2008/0236088 A1 | 10/2008 | Hannig |
| 2008/0244882 A1 | 10/2008 | Woxman et al. |
| 2009/0014401 A1 | 1/2009 | Tallman |
| 2009/0019806 A1 | 1/2009 | Muehlebach |
| 2009/0064624 A1 | 3/2009 | Sokol |
| 2010/0028592 A1 | 2/2010 | Barkdoll et al. |
| 2010/0083603 A1 | 4/2010 | Goodwin |
| 2010/0104354 A1 | 4/2010 | Spalding |
| 2010/0173122 A1 | 7/2010 | Susnjara |
| 2010/0289389 A1 | 11/2010 | Crabtree, II |
| 2011/0023303 A1 | 2/2011 | Pervan et al. |
| 2011/0225921 A1 | 9/2011 | Schulte |
| 2011/0225922 A1 | 9/2011 | Pervan et al. |
| 2011/0280655 A1 | 11/2011 | Maertens et al. |
| 2011/0283650 A1 | 11/2011 | Pervan et al. |
| 2012/0009383 A1 | 1/2012 | Hardesty |
| 2012/0027967 A1 | 2/2012 | Maertens et al. |
| 2012/0073235 A1 | 3/2012 | Hannig |
| 2012/0124932 A1 | 5/2012 | Schulte et al. |
| 2012/0145845 A1 | 6/2012 | Hightower |
| 2012/0180416 A1 | 7/2012 | Perra et al. |
| 2012/0279161 A1 | 11/2012 | Hakansson et al. |
| 2012/0286637 A1 | 11/2012 | Fehre |
| 2013/0008117 A1 | 1/2013 | Pervan |
| 2013/0014463 A1 | 1/2013 | Pervan |
| 2013/0048632 A1 | 2/2013 | Chen |
| 2013/0071172 A1 | 3/2013 | Maertens et al. |
| 2013/0081349 A1 | 4/2013 | Pervan et al. |
| 2013/0097846 A1 | 4/2013 | Pettigrew et al. |
| 2013/0111845 A1 | 5/2013 | Pervan et al. |
| 2013/0170904 A1 | 7/2013 | Cappelle et al. |
| 2013/0232905 A2 | 9/2013 | Pervan |
| 2013/0287484 A1 | 10/2013 | Phillips |
| 2014/0013919 A1 | 1/2014 | Gerke et al. |
| 2014/0055018 A1 | 2/2014 | Shein et al. |
| 2014/0111076 A1 | 4/2014 | Devos et al. |
| 2014/0286701 A1 | 9/2014 | Sauer |
| 2014/0294498 A1 | 10/2014 | Logan |
| 2015/0034522 A1 | 2/2015 | Itou et al. |
| 2015/0035422 A1 | 2/2015 | Hakansson et al. |
| 2015/0078807 A1 | 3/2015 | Brännström et al. |
| 2015/0078819 A1 | 3/2015 | Derelv et al. |
| 2015/0196118 A1 | 7/2015 | Derelv |
| 2015/0198191 A1 | 7/2015 | Boo |
| 2015/0230600 A1 | 8/2015 | Schulte |
| 2015/0252573 A1* | 9/2015 | Devos ............ E04C 2/38 52/582.2 |
| 2015/0330088 A1 | 11/2015 | Derelov |
| 2015/0368896 A1 | 12/2015 | Schulte |
| 2016/0000220 A1 | 1/2016 | Devos et al. |
| 2016/0007751 A1 | 1/2016 | Derelv |
| 2016/0145029 A1 | 5/2016 | Ranade et al. |

(56) References Cited

U.S. PATENT DOCUMENTS

| | | |
|---|---|---|
| 2016/0174704 A1 | 6/2016 | Boo et al. |
| 2016/0186925 A1 | 6/2016 | Bettin |
| 2016/0192775 A1 | 7/2016 | Andersson |
| 2016/0270531 A1 | 9/2016 | Derelv |
| 2016/0281368 A1 | 9/2016 | Pervan et al. |
| 2017/0079433 A1 | 3/2017 | Derelov et al. |
| 2017/0089379 A1 | 3/2017 | Pervan |
| 2017/0097033 A1 | 4/2017 | Hakansson et al. |
| 2017/0159291 A1 | 6/2017 | Derelv |
| 2017/0208938 A1 | 7/2017 | Derelv et al. |
| 2017/0227031 A1 | 8/2017 | Boo |
| 2017/0227032 A1 | 8/2017 | Fridlund |
| 2017/0227035 A1 | 8/2017 | Fridlund |
| 2017/0234346 A1 | 8/2017 | Fridlund |
| 2017/0298973 A1 | 10/2017 | Derelv |
| 2017/0328072 A1 | 11/2017 | Hannig |
| 2017/0340107 A1 | 11/2017 | Shen |
| 2017/0360193 A1 | 12/2017 | Boo et al. |
| 2018/0080488 A1 | 3/2018 | Derelv |
| 2018/0087552 A1 | 3/2018 | Derelv et al. |
| 2018/0112695 A1 | 4/2018 | Boo et al. |
| 2018/0119717 A1 | 5/2018 | Derelv |
| 2018/0202160 A1 | 7/2018 | Derelv |
| 2018/0283430 A1 | 10/2018 | Leistert |
| 2018/0328396 A1 | 11/2018 | Fransson et al. |
| 2019/0048596 A1 | 2/2019 | Pervan |
| 2019/0113061 A1 | 4/2019 | Hakansson et al. |
| 2019/0166989 A1 | 6/2019 | Boo et al. |
| 2019/0191870 A1 | 6/2019 | Derelv |
| 2019/0195256 A1 | 6/2019 | Derelv |
| 2019/0289999 A1 | 9/2019 | Derelv et al. |
| 2019/0320793 A1 | 10/2019 | Boo |
| 2019/0323532 A1 | 10/2019 | Boo |
| 2019/0323533 A1 | 10/2019 | Boo |
| 2019/0323534 A1 | 10/2019 | Derelv |
| 2019/0323535 A1 | 10/2019 | Derelv |
| 2020/0003242 A1 | 1/2020 | Brnnstrm et al. |
| 2020/0055126 A1 | 2/2020 | Fridlund |
| 2020/0069048 A1 | 3/2020 | Derelv et al. |
| 2020/0069049 A1 | 3/2020 | Derelv et al. |
| 2020/0102978 A1 | 4/2020 | Fridlund |
| 2020/0121076 A1 | 4/2020 | Derelov et al. |
| 2020/0214447 A1 | 7/2020 | Derelov et al. |
| 2020/0300284 A1 | 9/2020 | Pervan |
| 2020/0337455 A1 | 10/2020 | Boo et al. |
| 2020/0340513 A1 | 10/2020 | Derelv |
| 2021/0047840 A1 | 2/2021 | Pervan |
| 2021/0079650 A1 | 3/2021 | Derelov |
| 2021/0148392 A1 | 5/2021 | Brnnstrm et al. |
| 2021/0180630 A1 | 6/2021 | Bruno et al. |
| 2021/0190112 A1 | 6/2021 | Derelv |
| 2021/0207635 A1 | 7/2021 | Hkansson et al. |
| 2021/0222716 A1 | 7/2021 | Derelv et al. |
| 2021/0262507 A1 | 8/2021 | Svensson et al. |
| 2021/0262508 A1 | 8/2021 | Svensson et al. |
| 2021/0276108 A1 | 9/2021 | Derelv et al. |
| 2021/0285480 A1 | 9/2021 | Derelv et al. |
| 2021/0310257 A1 | 10/2021 | Boo |
| 2021/0381251 A1 | 12/2021 | Svensson |
| 2022/0018373 A1 | 1/2022 | Boo |
| 2022/0049735 A1 | 2/2022 | Meijer |
| 2022/0213912 A1 | 7/2022 | Boo |
| 2022/0228615 A1 | 7/2022 | Sostar |
| 2022/0243751 A1 | 8/2022 | Brännström et al. |
| 2022/0252097 A1 | 8/2022 | Rydsjöet al. |
| 2022/0408921 A1 | 12/2022 | Meijer |
| 2023/0080262 A1 | 3/2023 | Hkansson et al. |

FOREIGN PATENT DOCUMENTS

| | | |
|---|---|---|
| CH | 365507 A | 11/1962 |
| CH | 685276 A5 | 5/1995 |
| CH | 696889 A5 | 1/2008 |
| CH | 698988 B1 | 12/2009 |
| CH | 705082 A2 | 12/2012 |
| CN | 1922053 A | 2/2007 |
| CN | 101099618 A | 1/2008 |
| CN | 101484651 A | 7/2009 |
| CN | 102917616 A | 2/2013 |
| CN | 203424576 U | 2/2014 |
| CN | 103649439 A | 3/2014 |
| CN | 103748298 A | 4/2014 |
| CN | 103957748 A | 7/2014 |
| CN | 203718365 U | 7/2014 |
| CN | 105041806 A | 11/2015 |
| CN | 105324544 A | 2/2016 |
| CN | 105518316 A | 4/2016 |
| CN | 205780086 U | 12/2016 |
| CN | 106460901 A | 2/2017 |
| CN | 107002411 A | 8/2017 |
| CN | 107002732 A | 8/2017 |
| CN | 107529889 A | 1/2018 |
| DE | 1107910 B | 5/1961 |
| DE | 2414104 A1 | 10/1975 |
| DE | 2514357 A1 | 10/1975 |
| DE | 3103281 A1 | 8/1982 |
| DE | 0228872 A1 | 10/1985 |
| DE | 4229115 A1 | 3/1993 |
| DE | 9417168 U1 | 2/1995 |
| DE | 19831936 A1 | 2/1999 |
| DE | 29820031 U1 | 2/1999 |
| DE | 19805538 A1 | 8/1999 |
| DE | 20304761 U1 | 4/2004 |
| DE | 29924630 U1 | 5/2004 |
| DE | 202005019986 U1 | 2/2006 |
| DE | 202004017486 U1 | 4/2006 |
| DE | 202009008825 U1 | 10/2009 |
| DE | 102008035293 A1 | 2/2010 |
| DE | 102009041142 A1 | 3/2011 |
| DE | 102011057018 A1 | 6/2013 |
| DE | 102013008595 A1 | 11/2013 |
| DE | 102015103429 A1 | 10/2015 |
| DE | 102014110124 A1 | 1/2016 |
| DE | 202017101856 U1 | 4/2017 |
| EP | 0060203 A2 | 9/1982 |
| EP | 0357129 A1 | 3/1990 |
| EP | 0362968 A1 | 4/1990 |
| EP | 0675332 A2 | 10/1995 |
| EP | 0871156 A2 | 10/1998 |
| EP | 1048423 A2 | 11/2000 |
| EP | 1650375 A1 | 4/2006 |
| EP | 1671562 A1 | 6/2006 |
| EP | 1863984 A1 | 12/2007 |
| EP | 1922954 A1 | 5/2008 |
| EP | 2017403 A2 | 1/2009 |
| EP | 2333353 A2 | 6/2011 |
| EP | 2487373 A1 | 8/2012 |
| EP | 3031998 A1 | 6/2016 |
| FR | 2517187 A1 | 6/1983 |
| FR | 2597173 A1 | 10/1987 |
| FR | 2602013 A1 | 1/1988 |
| GB | 0245332 A | 1/1926 |
| GB | 0799155 A | 8/1958 |
| GB | 1022377 A | 3/1966 |
| GB | 2163825 A | 3/1986 |
| GB | 2315988 A | 2/1998 |
| GB | 2445954 A | 7/2008 |
| GB | 2482213 A | 1/2012 |
| GB | 2520927 A | 6/2015 |
| JP | 53-113160 U | 9/1978 |
| JP | 06-022606 U | 3/1994 |
| JP | 2003-239921 A | 8/2003 |
| JP | 2008-518130 A | 5/2008 |
| JP | 2014-523996 A | 9/2014 |
| KR | 10-1147274 B1 | 5/2012 |
| KR | 10-2014-0042314 A | 4/2014 |
| WO | 87/07339 A1 | 12/1987 |
| WO | 90/07066 A2 | 6/1990 |
| WO | 99/22150 A1 | 5/1999 |
| WO | 99/41508 A2 | 8/1999 |
| WO | 00/66856 A1 | 11/2000 |
| WO | 01/53628 A1 | 7/2001 |
| WO | 02/55809 A1 | 7/2002 |
| WO | 02/55810 A1 | 7/2002 |

(56) References Cited

FOREIGN PATENT DOCUMENTS

| WO | 03/83234 | A1 | 10/2003 |
|---|---|---|---|
| WO | 2004/079130 | A1 | 9/2004 |
| WO | 2005/068747 | A1 | 7/2005 |
| WO | 2006/043893 | A1 | 4/2006 |
| WO | 2006/104436 | A1 | 10/2006 |
| WO | 2007/015669 | A2 | 2/2007 |
| WO | 2008/004960 | A2 | 1/2008 |
| WO | 2008/017281 | A1 | 2/2008 |
| WO | 2008/150234 | A1 | 12/2008 |
| WO | 2009/136195 | A1 | 11/2009 |
| WO | 2010/087752 | A1 | 8/2010 |
| WO | 2011/151758 | A2 | 12/2011 |
| WO | 2012/095454 | A1 | 7/2012 |
| WO | 2012/154113 | A1 | 11/2012 |
| WO | 2013/009257 | A1 | 1/2013 |
| WO | 2013/025163 | A1 | 2/2013 |
| WO | 2013/080160 | A1 | 6/2013 |
| WO | 2013/118075 | A1 | 8/2013 |
| WO | 2014/072080 | A1 | 5/2014 |
| WO | 2014/121410 | A1 | 8/2014 |
| WO | 2015/015603 | A1 | 2/2015 |
| WO | 2015/038059 | A1 | 3/2015 |
| WO | 2015/105449 | A1 | 7/2015 |
| WO | 2015/105450 | A1 | 7/2015 |
| WO | 2015/105451 | A1 | 7/2015 |
| WO | 2016/099396 | A1 | 6/2016 |
| WO | 2016/175701 | A1 | 11/2016 |
| WO | 2016/187533 | A1 | 11/2016 |
| WO | 2017/131574 | A1 | 8/2017 |
| WO | 2017/138874 | A1 | 8/2017 |
| WO | 2018/004435 | A1 | 1/2018 |
| WO | 2018/080387 | A1 | 5/2018 |
| WO | 2019/125291 | A1 | 6/2019 |
| WO | 2019/125292 | A1 | 6/2019 |

OTHER PUBLICATIONS

International Preliminary Report on Patentability received for PCT Patent Application No. PCT/SE2019/050359, mailed on Oct. 29, 2020, 11 pages.
International Search Report and Written Opinion mailed May 31, 2019 in PCT/SE2019/050359, ISA/SE, Patent-och registreringsverket, Stockholm, SE, 15 pages.
Notice of Allowance received for Chinese Patent Application No. 201980038880.2, mailed on Oct. 21, 2022, 3 pages (2 pages of English Translation and 1 page of Original Document).
Office Action received for Chinese Patent Application No. 201980038880.2, mailed on Apr. 28, 2022, 14 pages (7 pages of English Translation and 5 pages of Original Document).
Office Action received for Chinese Patent Application No. 201980038880.2, mailed on Nov. 16, 2021, 14 pages (7 pages of English Translation and 7 pages of Original Document).
Office Action received for European Application No. 19789380, mailed on Oct. 17, 2023, 3 pages.
Office Action received for Japanese Patent Application No. 2020-556959, mailed on Feb. 3, 2023, 6 pages (3 pages of English Translation and 3 pages of Original Document).
Office Action received for Japanese Patent Application No. 2020-556959, mailed on May 16, 2023, 5 pages (2 pages of English Translation and 3 pages of Original Document).
Supplementary European Search Report and Search Opinion received for EP Application No. 19789380, mailed on Dec. 17, 2021, 8 pages.
U.S. Appl. No. 17/398,416, Thomas Meijer, filed Aug. 10, 2021.
U.S. Appl. No. 17/514,055, Marko Sostar, filed Oct. 29, 2021.
U.S. Appl. No. 17/665,160, Oscar Rydsjö, filed Feb. 4, 2022.
U.S. Appl. No. 17/784,341, Johan Svensson, filed Jun. 10, 2022.
U.S. Appl. No. 17/847,655, Thomas Meijer, filed Jun. 23, 2022.
U.S. Appl. No. 17/870,215, Peter Derelöv, filed Jul. 21, 2022.
U.S. Appl. No. 17/959,010, Mindaugas Zacharenko, filed Oct. 3, 2022.
U.S. Appl. No. 18/058,037, Peter Derelöv, filed Nov. 22, 2022.
U.S. Appl. No. 18/191,404, Thomas Meijer, filed Mar. 28, 2023.
U.S. Appl. No. 18/239,924, Niclas Håkansson, filed Aug. 30, 2023.
U.S. Appl. No. 18/422,368, Christian Boo, filed Jan. 25, 2024.
U.S. Appl. No. 18/422,425, Christian Boo, filed Jan. 25, 2024.
U.S. Appl. No. 18/440,330, Thomas Meijer, filed Feb. 13, 2024.
U.S. Appl. No. 18/271,460, Peter Derelöv, filed Jul. 9, 2023.
U.S. Appl. No. 18/766,880, Thomas Meijer, filed Jul. 9, 2024.
U.S. Appl. No. 19/048,028, Oscar Rydsjö, filed Feb. 7, 2025.

* cited by examiner

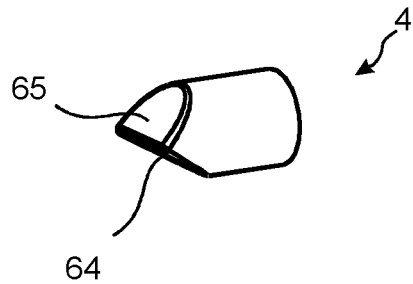
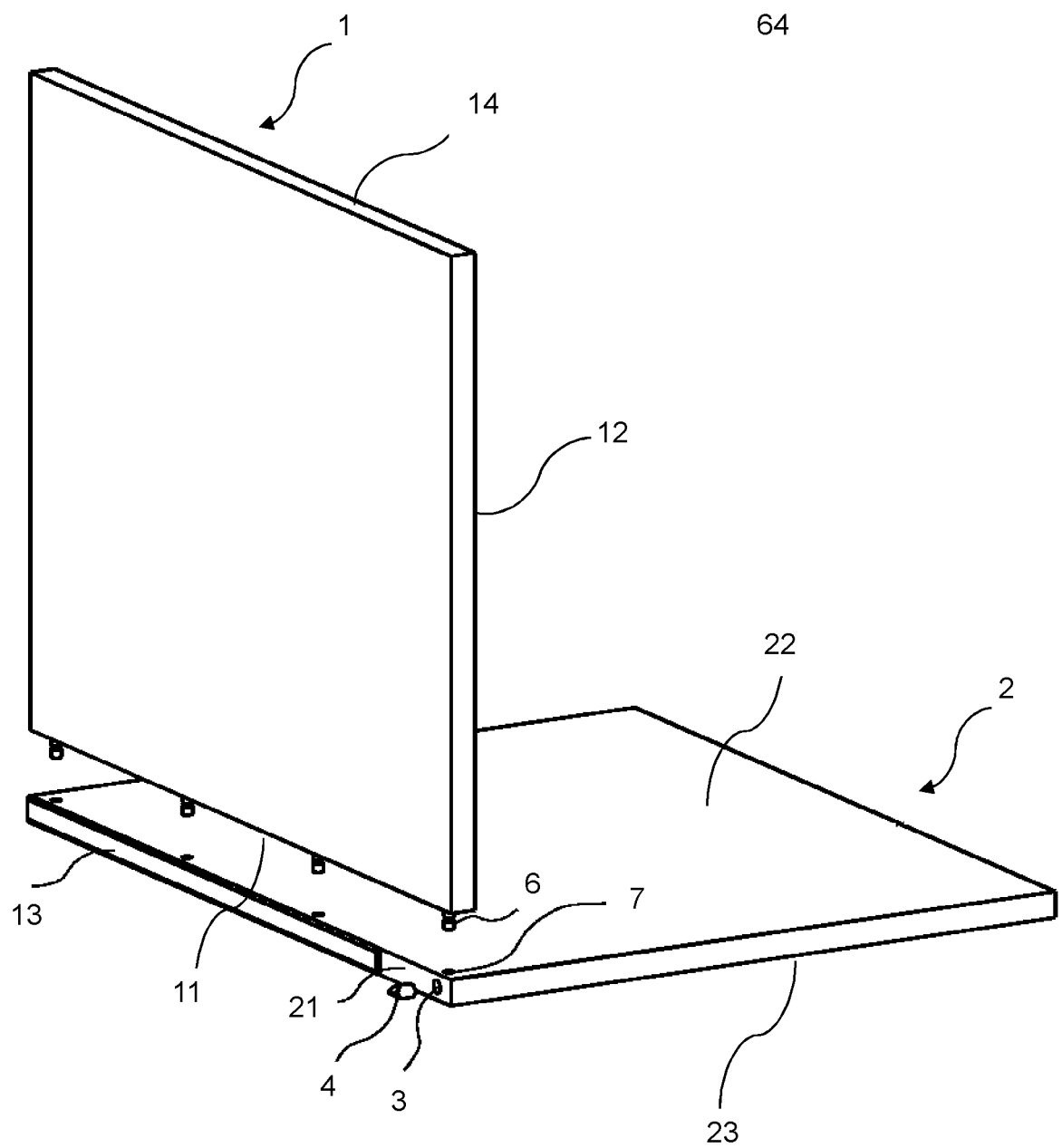

SYMMETRIC TONGUE AND T-CROSS

CROSS REFERENCE TO RELATED APPLICATIONS

The present application is a continuation of U.S. application Ser. No. 18/058,037, filed on Nov. 22, 2022, which is a continuation of U.S. application Ser. No. 16/386,874, filed on Apr. 17, 2019, now U.S. Pat. No. 11,536,307, which claims the benefit of Swedish Application No. 1850441-5, filed on 18 Apr. 2018. The entire contents of U.S. application Ser. No. 18/058,037, U.S. application Ser. No. 16/386,874 and Swedish Application No. 1850441-5 are hereby incorporated herein by reference in their entirety.

TECHNICAL FIELD

Embodiments of the present invention relate to panels configured to be locked together with a mechanical locking device. The panels may be floorboards to be locked together to obtain a floor product, or panels that may be assembled and locked together to obtain a furniture product, such as a bookshelf, a cupboard, a wardrobe, a box, a drawer, or a furniture component and may thereafter be dismantled. The mechanical locking device may comprise a flexible tongue.

TECHNICAL BACKGROUND

A furniture product provided with a mechanical locking device is known in the art, as evidenced by WO2015/038059. The furniture product comprises a first panel connected perpendicular to a second panel by a mechanical locking device comprising a flexible tongue in an insertion groove.

The above description of various known aspects is the applicant's characterization of such, and is not an admission that any of the above description is considered as prior art.

Embodiments of the present invention address a need to provide panels that can be assembled and dismantled.

SUMMARY

It is an object of certain aspects of the present invention to provide an improvement over the above-described techniques and known art; particularly, to achieve a set that could be dismantled/disassembled after assembly without damaging the mechanical locking device, such that the set yet again could be assembled.

It is an object of at least certain embodiments and aspects of the present invention to provide an improvement over the above-described techniques and known art.

A further object of at least certain aspects of the present invention is to facilitate assembling of panels configured to be assembled without the need of using any tools.

A further object of at least certain aspects of the present invention is to facilitate disassembling of panels configured to be assembled.

A further object of at least certain aspects of the present invention is to facilitate assembling and disassembling of panels configured to be assembled with a locking device that is easy to manufacture and to use.

A further object of at least certain aspects of the present invention is to facilitate a method of disassembling assembled panels.

A further object of at least certain aspects of the present invention is to facilitate assembling of panels configured to be assembled with a locking device that is easy to use and install and which reduces the risk of incorrect installation thereof.

A further object of at least certain aspects of the present invention is to facilitate assembling of panels configured to be assembled in a more stable and aesthetic way.

At least some of these and other objects and advantages that will be apparent from the description have been achieved by a set comprising a first panel, a second panel and a mechanical locking device for locking the first panel to the second panel, wherein the first panel comprises a first edge surface and a first panel surface and the second panel comprises a second edge surface and a second panel surface, characterized in that the mechanical locking device comprises an insertion groove at the second edge surface, a flexible tongue positioned in the insertion groove and an edge tongue comprising a tongue groove, that the flexible tongue comprises a first locking surface and a second locking surface, that the first locking surface is configured to cooperate with the tongue groove for locking of the first panel to the second panel in a first direction when the flexible tongue is positioned in the insertion groove in a first orientation, and that the second locking surface of the flexible tongue is configured to cooperate with the tongue groove for a locking of the first panel to the second panel in a first direction when the flexible tongue is positioned in the insertion groove in a second orientation.

The first locking surface and the second locking surface may be essentially symmetrically positioned on the flexible tongue.

An angle between the first and second locking surface may be within the range of about 90° to about 180°, preferably within the range of about 150° to about 175°, or preferably about 158°.

The flexible tongue may comprise a guiding surface configured to cooperate with the edge tongue during a displacement of the first panel relative to the second panel.

The guiding surface may in a first end be connected to the first locking surface and in a second end be connected to the second locking surface.

The guiding surface may have a curved shape.

The guiding surface may have the shape of a circular segment.

The curved shape of the guiding surface may have a radius between the first and second locking surfaces within the range of about 0.5 mm to about 3 mm, preferably within the range of 1 mm to 2 mm, or preferably about 1.5 mm.

The flexible tongue may have a thickness T and the curved shape of the guiding surface may have a radius between the first and second locking surfaces within the range of about 0.2×T to 1.2×T or about 0.4×T to about 0.8×T, or 0.6×T.

The guiding surface may be configured to cooperate with a curved shape surface of a disassembling tool, wherein the disassembling tool preferably has a circular cross section.

The flexible tongue may have a support surface positioned opposite to the guiding surface, wherein the support surface may have a curved shape with a radius within the range of about 25 mm to about 50 mm, preferably within the range of 30 mm to 45 mm, or preferably about 37 mm.

The curved shape of the support surface may have a radius that is smaller than a radius of a bottom surface of the insertion groove.

The first or second direction for locking of the first panel to the second panel may be parallel and/or perpendicular to the second panel surface.

The edge tongue may be a rod-shaped element at the first edge surface and at a third edge surface of the first panel and the mechanical locking device may comprise a first element groove at the second panel surface and a second element groove at a third panel surface of the second panel, wherein the rod-shaped element may comprise the tongue groove and may be configured to be inserted into the first or second element groove, wherein the first element groove may extend from the second panel surface to the insertion groove and the second element groove may extend from the third panel surface to the insertion groove, the first locking surface of the flexible tongue may be configured to cooperate with the tongue groove for a locking of the first panel to the second panel in a first direction which is perpendicular to the first panel surface when it is inserted into the first element groove and the first edge surface is arranged against the first panel surface; and the second locking surface of the flexible tongue may be configured to cooperate with the tongue groove for locking of the first panel to the second panel in a first direction which is perpendicular to the first panel surface when it is inserted into the second element groove and the third edge surface is arranged against the third panel surface.

A first crosscut of the rod-shaped element, in a plane parallel to the first or second panel surface, may have a circular shape or a rectangular shape.

The mechanical locking device may be configured to automatically lock the first panel to the second panel when the rod-shaped element is inserted into the first or second element groove and the first edge surface is arranged against the first panel surface and/or the third edge surface is arranged against the second panel surface.

The rod-shaped element may have a longitudinal shape with a length direction which may be parallel to the first panel surface of the first panel.

In one aspect the locking surface and the adjacent sides of the flexible tongue may preferably have edges that are rounded, i.e., have a radius, which results in that the tongue is easier to insert and move in the insertion groove, also reducing the risk for fibers falling off from the insertion groove when the flexible tongue is inserted and moved in the insertion groove.

According to one aspect there is provided a flexible tongue comprising a first locking surface and a second locking surface. The first locking surface is configured to cooperate with a tongue groove for locking of a first panel to a second panel in a first direction when the flexible tongue is positioned in an insertion groove in a first orientation. The second locking surface of the flexible tongue is configured to cooperate with the tongue groove for a locking of the first panel to the second panel in a first direction when the flexible tongue is positioned in the insertion groove in a second orientation.

The first locking surface and the second locking surface may be essentially symmetrically positioned on the flexible tongue.

An angle between the first and second locking surface may be within the range of about 90° to about 180°, preferably within the range of about 150° to about 175°, or preferably about 158°.

The flexible tongue may comprise a guiding surface.

The guiding surface may in a first end be connected to the first locking surface and in a second end be connected to the second locking surface.

The guiding surface may have a curved shape.

The guiding surface may have the shape of a circular segment.

The curved shape of the guiding surface may have a radius between the first and second locking surfaces within the range of about 0.5 mm to about 3 mm, preferably within the range of 1 mm to 2 mm, or preferably about 1.5 mm.

The flexible tongue may have a thickness T and the curved shape of the guiding surface may have a radius between the first and second locking surfaces within the range of about 0.2×T to 1.2×T or about 0.4×T to about 0.8×T, or 0.6×T.

According to an aspect the core of the first panel and/or of the second panel may be a wood-based core, preferably made of MDF, HDF, OSB, WPC, plywood, or particleboard. The core may also be a plastic core comprising thermosetting plastic or thermoplastic e.g., vinyl, PVC, PU or PET. The plastic core may comprise fillers.

The first panel and/or the second panel may also be of solid wood.

The second panel may also be of metal, such as sheet metal.

The first panel and/or the second panel may be provided with a decorative layer, such as a foil or a veneer, on one or more surfaces.

BRIEF DESCRIPTION OF THE DRAWINGS

These and other aspects, features, and advantages of which embodiments of the invention are capable of, will be apparent and elucidated from the following description of embodiments and aspects of the present invention, reference being made to the accompanying drawings, in which FIG. 1A shows a 3D-view of an embodiment of the invention during assembling.

FIG. 1B shows an embodiment of the flexible tongue according to an embodiment of the invention.

DETAILED DESCRIPTION

Figure 2A:
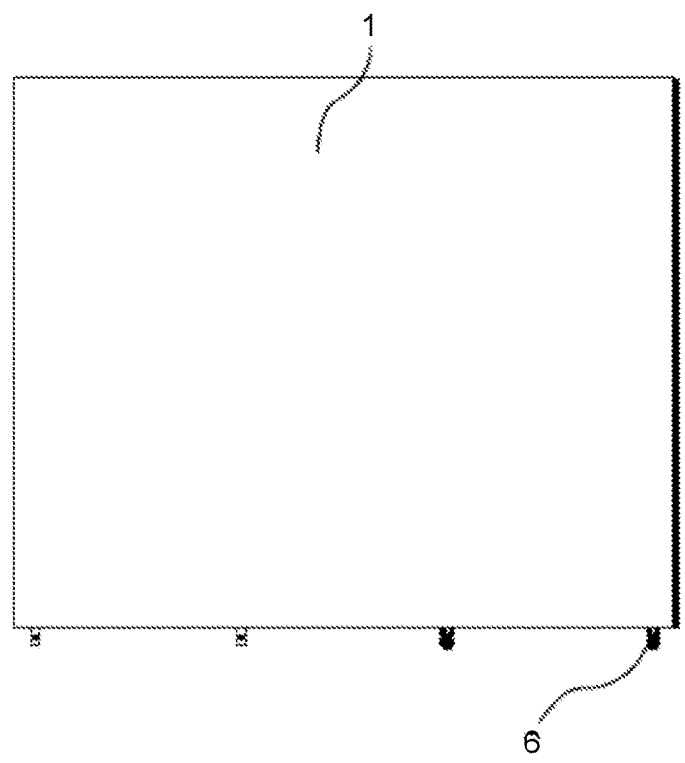
FIGS. 2A-2B show side views of an embodiment of the first panel according to an embodiment of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The terminology used herein is for the purpose of describing particular aspects of the disclosure only, and is not intended to limit the disclosure. As used herein, the singular forms "a", "an" and "the" are intended to include the plural forms as well, unless the context clearly indicates otherwise.

It should be noted that the word "comprising" does not necessarily exclude the presence of other elements or steps than those listed and the words "a" or "an" preceding an element do not exclude the presence of a plurality of such elements. It should further be noted that any reference signs do not limit the scope of the claims, that the example aspects may be implemented at least in part by means of both hardware and software, and that several "means", "units" or "devices" may be represented by the same item of hardware.

The different aspects, alternatives and embodiments of the invention disclosed herein can be combined with one or more of the other aspects, alternatives and embodiments described herein. Two or more aspects can be combined.

A first embodiment of the invention is shown, e.g., in FIGS. 1-8A and 9A-13B including a set comprising a first panel 1, a second panel 2 and a mechanical locking device for locking the first panel 1 to the second panel 2. The first panel 1 comprises a first edge surface 11 and a first panel surface 12. The second panel 2 comprises a second edge surface 21 and a second panel surface 22. The mechanical locking device further comprises an insertion groove 3 at the second edge surface 21, a flexible tongue 4 positioned in the insertion groove 3 and an edge tongue comprising a tongue groove 9. The flexible tongue 4 comprises a first locking surface 101 and a second locking surface 102. The first locking surface 101 is configured to cooperate with the tongue groove 9 for locking of the first panel 1 to the second panel 2 in a first direction when the flexible tongue 4 is positioned in the insertion groove 3 in a first orientation. The second locking surface 102 of the flexible tongue 4 is configured to cooperate with the tongue groove 9 for a locking of the first panel 1 to the second panel 2 in a first direction when the flexible tongue 4 is positioned in the insertion groove 3 in a second orientation.

The first panel 1 and the second panel 2 are preferably panels for a furniture product and may be a part of a frame of a furniture product.

For a furniture product, the set is preferably configured for locking the first panel 1 to the second panel 2 with the first panel surface 12 perpendicular or essentially perpendicular to the second panel surface 22.

Figure 8A:
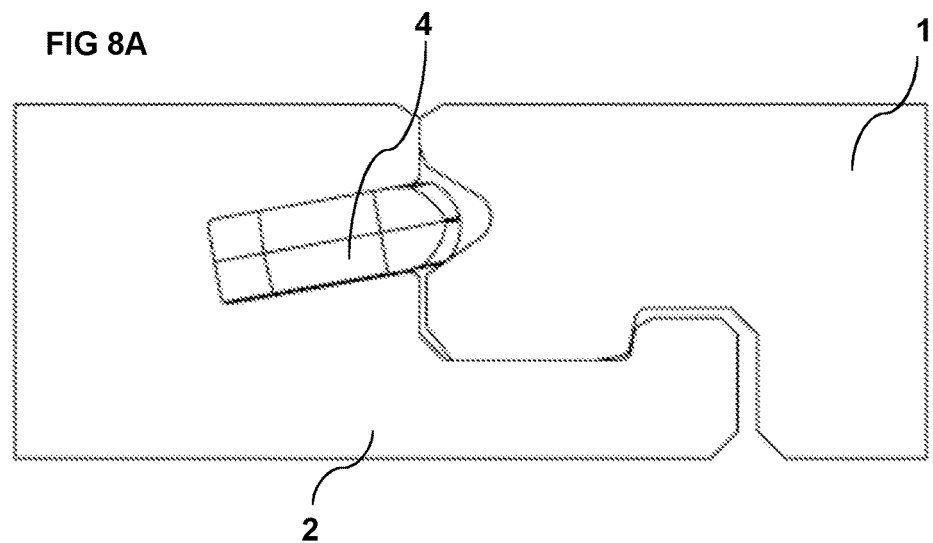
FIG. 8A shows a cross section of an embodiment of the first panel and the second panel in a locked position according to an embodiment of the invention.

The first panel 1 and the second panel 2 may also be floorboards, as illustrated in FIG. 8A, to be locked together to obtain a floor product.

FIG. 1A shows the first embodiment in a 3D view during assembling of a furniture product. The first panel may be assembled by displacing the first panel relative the second panel in a direction which is perpendicular to the second panel surface 22. The mechanical locking device may be configured to automatically lock the first panel 1 to the second panel 2 when the rod-shaped element 6 is inserted into the first element groove 7 and the first edge surface 11 is arranged against second panel surface 22. Embodiments are shown in WO 2018/080387. The entire contents of WO 2018/080387 are hereby expressly incorporated by reference.

An embodiment of the flexible tongue 4 is shown in FIG. 1B in a 3D view which is configured for an insertion groove 3 which may comprise a circular cross section. The flexible tongue may have a curved surface which preferably matches the circular cross section of the edge groove 3. A first part of the flexible tongue is configured to cooperate with the insertion groove and a second part is configured to cooperate with the recess 9 of the rod-shaped element 6. An advantage with this embodiment of the flexible tongue is that the size of the edge groove may be small. A small edge groove may have the advantage that the effect of the strength of the second edge of the second panel is limited or non-existent.

The second part may comprise a first bevel 65 which is configured to cooperate with the rod-shaped element 8 during assembling and a second bevel 64 which is configured to cooperate with the recess for the locking.

The flexible tongue may comprise a flexible material to enable compression and a displacement of the flexible tongue in the edge groove during assembling.

The flexible tongue may comprise an element which is flexible to enable compression and a displacement of the flexible tongue in the edge groove during assembling and another element which is less flexible in order to improve the locking strength.

A part of the curved surface of the flexible tongue 6 may be configured to be displaced against a surface, such as a cylindrical surface, of the edge groove 5.

The first edge surface 12 may comprise two or more of said rod shaped element and the second panel surface 3 may comprise two or more of said insertion groove 7, preferably arranged linearly, wherein each of the rod-shaped elements is configured to be inserted into one of the insertion grooves.

The first element groove 7 may be formed in the second panel surface 22 and in a core of the second panel 2.

The second panel surface 22 may comprise a decorative layer and the first element groove 7 may extend though the decorative layer.

The first element groove 7 may be formed by mechanical cutting, such as drilling.

An edge element 13, such as an edge band, is preferably attached to the second edge surface 21 for covering the insertion groove 3 and for reinforcing the second edge surface 21. The edge element 13 may be glued to the second edge surface 21 or attached by a mechanical locking device, which may comprise a part that protrudes from the edge element and is configured to be inserted into the insertion groove 3. The part may be attached to the insertion groove 3 by friction. The edge element 13 is in FIG. 1A partly removed in order to visualize the flexible tongue 4 and the insertion groove 3. The flexible tongue 4 is shown before it is positioned in the insertion groove 3. The insertion groove 3 may comprise a circular cross section.

Embodiments are shown in FIGS. 4A-4B and 6A-10 which comprise an embodiment of the insertion groove 3 which is a longitudinal groove that extends in a longitudinal direction of the second edge surface 21. Embodiments of the flexible tongue 4 for a longitudinal groove are shown in FIGS. 11-13. The first locking surface 101 and the second locking surface 102 may be essentially symmetrically positioned on the flexible tongue 4. An angle 50 between the first 101 and second 102 locking surface is within the range of about 90° to about 180°, preferably within the range of about 150° to about 175°, or preferably about 158°.

The flexible tongue 4 may comprise a guiding surface 103 configured to cooperate with the edge tongue during a displacement of the first panel 1 relative to the second panel 2.

The guiding surface 103 in a first end may be connected to the first locking surface 101 and in a second end may be connected to the second locking surface 102.

The guiding surface 103 may have a curved shape.

The guiding surface 103 may have the shape of a circular segment.

The curved shape of the guiding surface 103 may have a radius between the first 101 and second 102 locking surfaces within the range of about 0.5 mm to about 3 mm, preferably within the range of 1 mm to 2 mm, or preferably about 1.5 mm.

The flexible tongue 4 may have a thickness T and the curved shape of the guiding surface 103 may have a radius between the first 101 and second 102 locking surfaces within the range of about 0.2×T to 1.2×T or about 0.4×T to about 0.8×T, or 0.6×T.

Figure 9A:
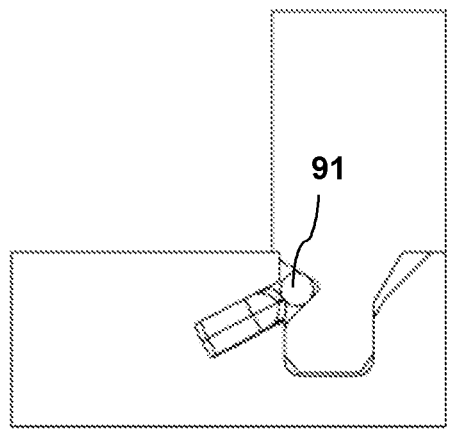
FIGS. 9A-9B show cross section of an embodiment of the first and the second panel, where a disassembling tool is used for disassembling of the first and second panel.

The guiding surface 103 may be configured to cooperate with a curved shape surface of a disassembling tool 91, wherein the disassembling tool may have a circular cross section, as shown in FIG. 9A.

Figure 9B:
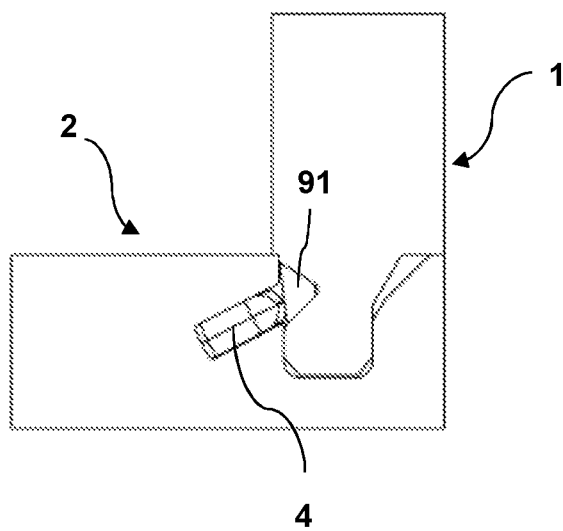

The guiding surface 103 may be configured to cooperate with a disassembling tool 91, wherein the disassembling tool may have a triangular cross section, as shown in FIG. 9B.

The flexible tongue 4 may have a support surface 104 positioned opposite to the guiding surface 103, wherein the support surface 104 may have a curved shape with a radius within the range of about 25 mm to about 50 mm, preferably within the range of 30 mm to 45 mm, or preferably about 37 mm.

Figure 4A:
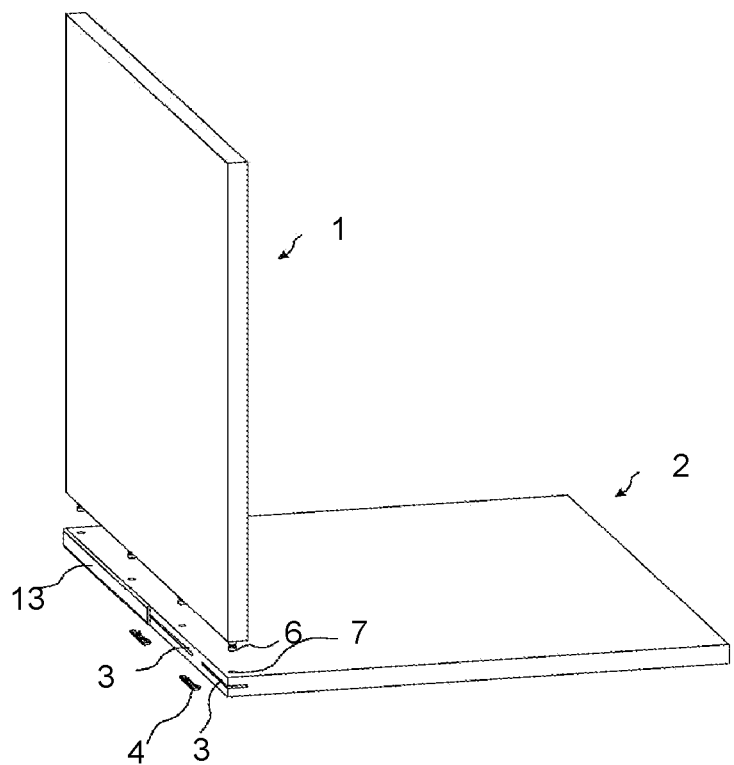
FIG. 4A shows a 3D-view of an embodiment of the invention during assembling.
Figure 4B:
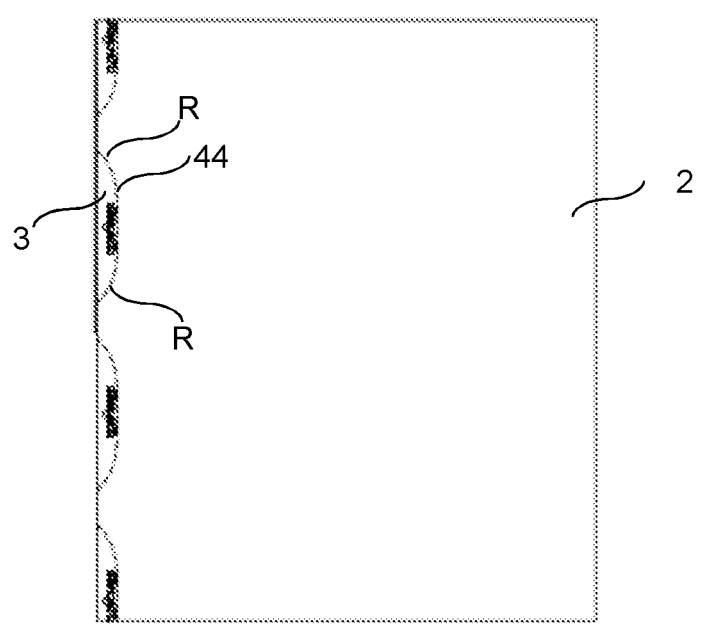
FIG. 4B shows a cross-section of an embodiment of the second panel.

The curved shape of the support surface 104 may have a radius R which is smaller or the same as a radius of a bottom surface 44 of the insertion groove 3, as illustrated in FIG. 4B.

The flexible tongue 4 may comprise a bendable part 61, preferably a first bendable part and a second bendable part. The flexible tongue 4 preferably comprises a recess 63 at each of said bendable part. An advantage with this embodiment of the flexible tongue is that a stronger spring force may be obtained which may provide a stronger locking. A disadvantage for some embodiments of the second panel is that the size of the insertion groove 3 may have to be larger which may weaken the second edge surface 21 of the second panel 2.

The flexible tongue may comprise a side 106, with a beveled or rounded shape. The side 106 may be configured to guide the insertion tool 91 during insertion into the tongue groove 9, see FIG. 9B.

The flexible tongue may comprise a protruding friction element 107 on the first and/or second bendable part 61. The size of the friction element 107 does not have to be the same on the first and second bendable part, but the size of the friction element 107 may be bigger on one side, which facilitates the movement of the tongue 4 sideways in the insertion groove 3.

Figure 11A:
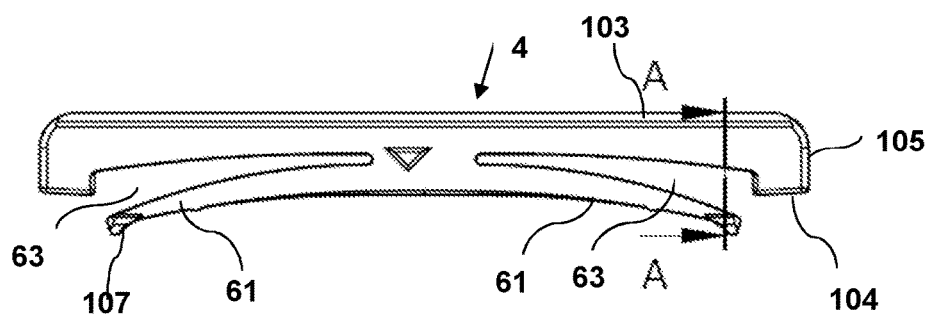
FIGS. 11A-11E shows different views of a flexible tongue according to an embodiment of the invention.
Figure 11B:
Figure 11C:
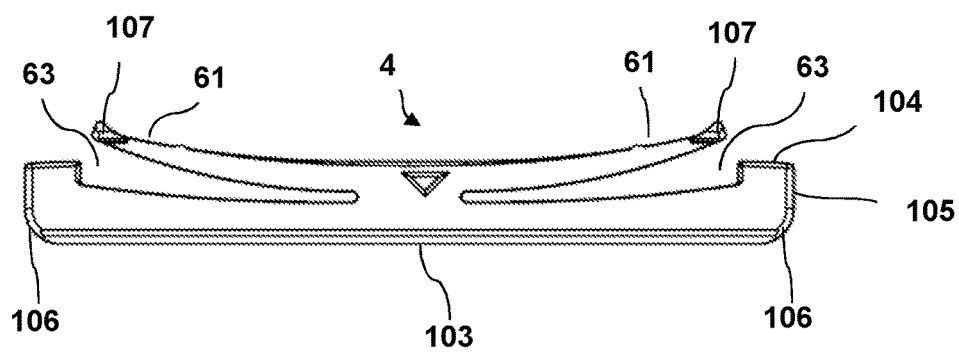
Figure 11D:
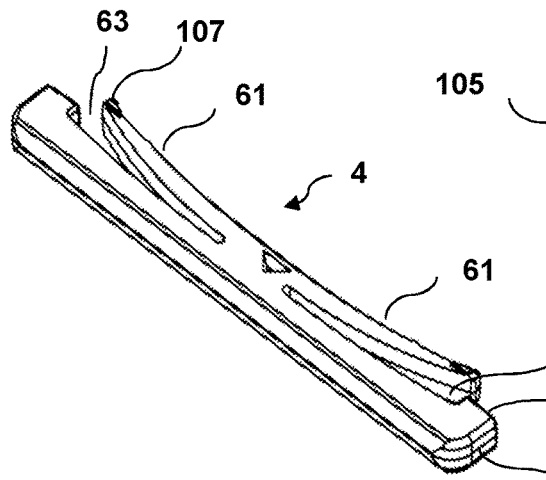
Figure 11E:
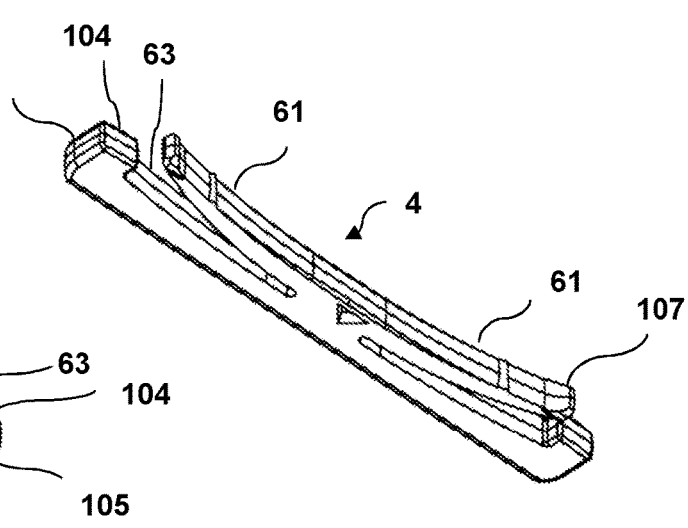
Figure 12A:
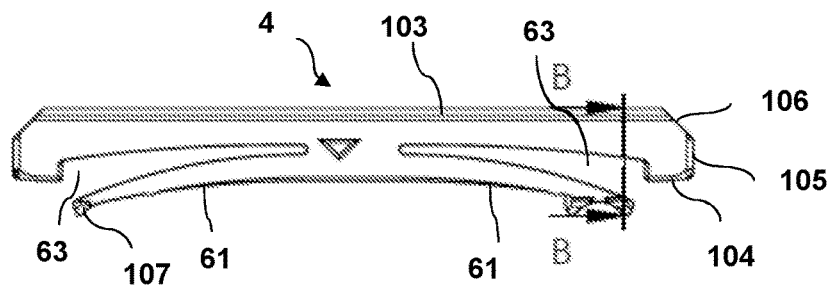
FIGS. 12A-12E shows different views of a flexible tongue according to an embodiment of the invention.
Figure 12B:
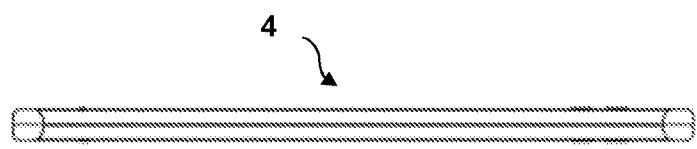
Figure 12C:
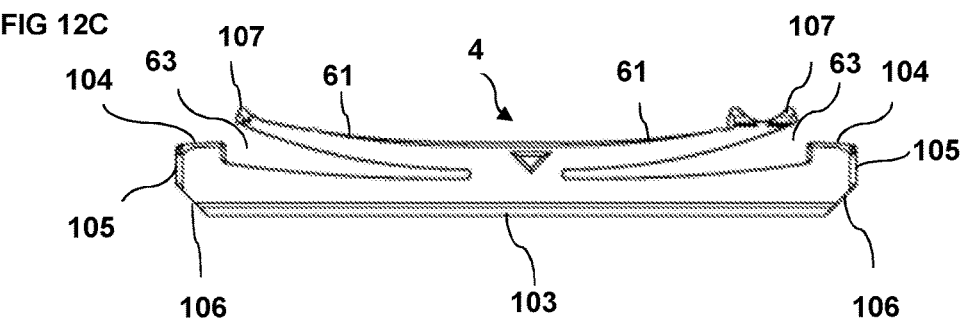
Figure 12D:
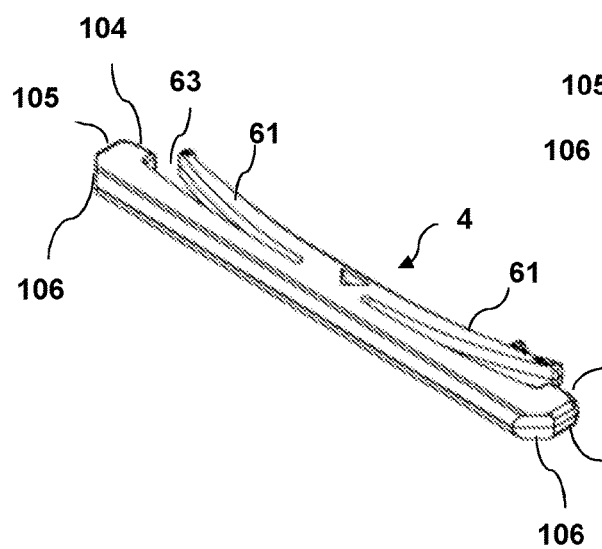
Figure 12E:
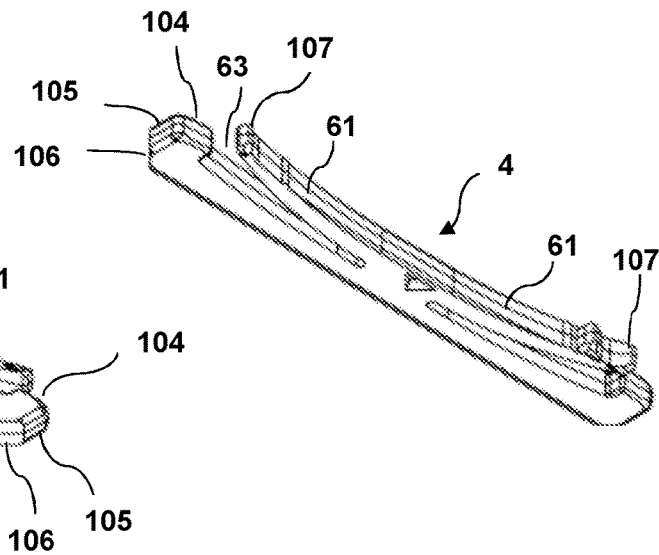
Figure 13A:
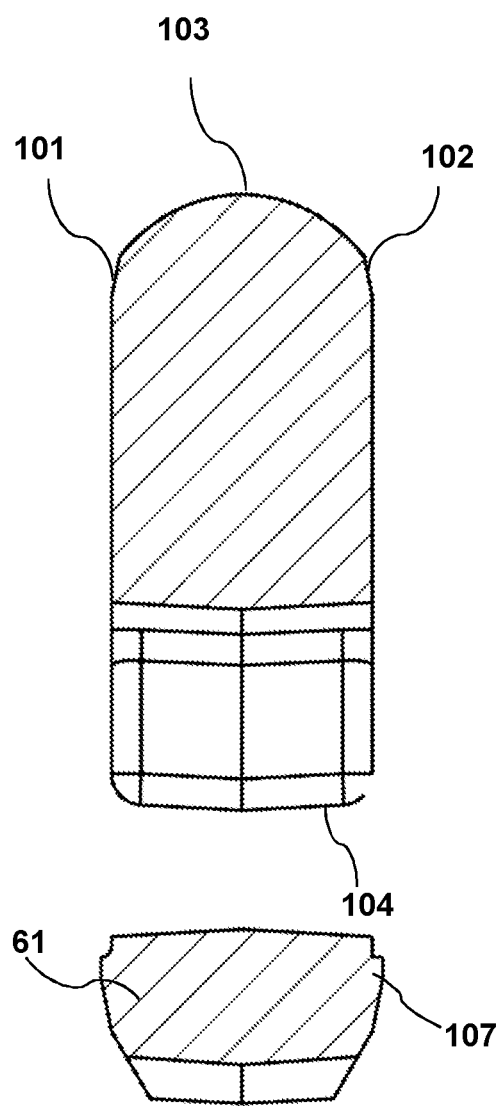
FIGS. 13A-13B show enlargements of a cross section A-A or B-B of part of the embodiments shown in FIGS. 11A-11E and 12A-12E.
Figure 13B:
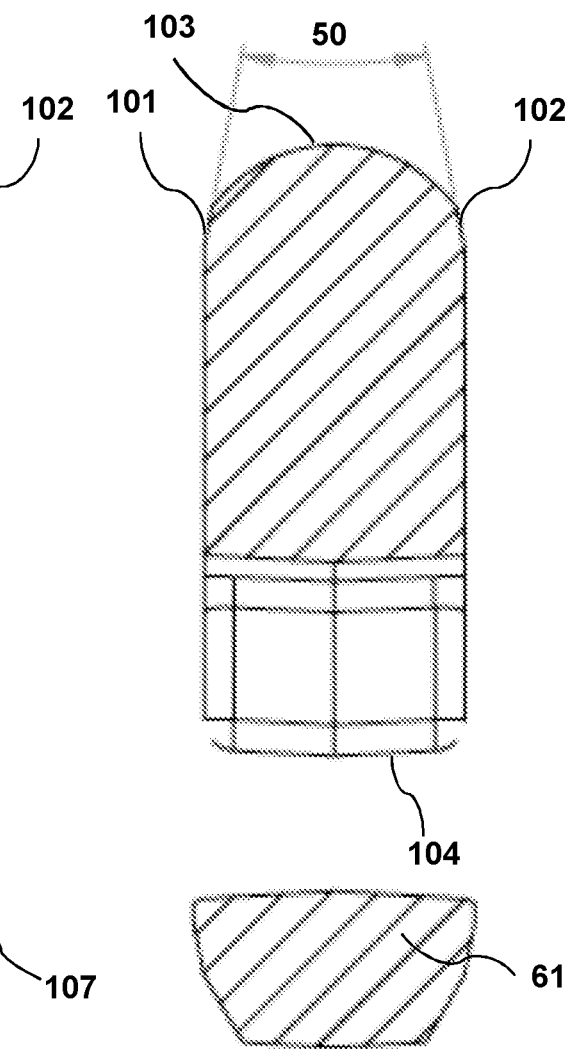

FIG. 13A shows enlargements of a cross section A-A indicated FIG. 11A. FIG. 13B shows enlargements of a cross section B-B indicated FIG. 12A. The cross-section A-A extends through the protruding friction element 107. The cross-section B-B is a side of the protruding friction element 107.

The first edge surface 11 may comprise two or more of said rod-shaped element 6 and the second panel surface 22 may comprise two or more of said first element groove 7, preferably arranged linearly, wherein each of the rod-shaped elements 6 is configured to be inserted into one of the first element grooves 7.

Figure 2B:
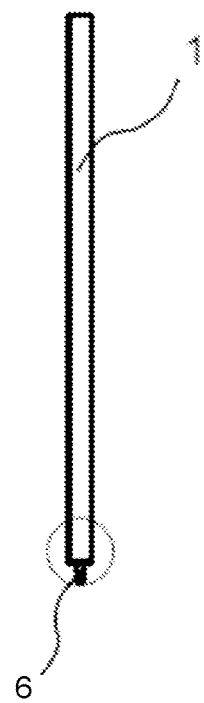
Figure 2C:
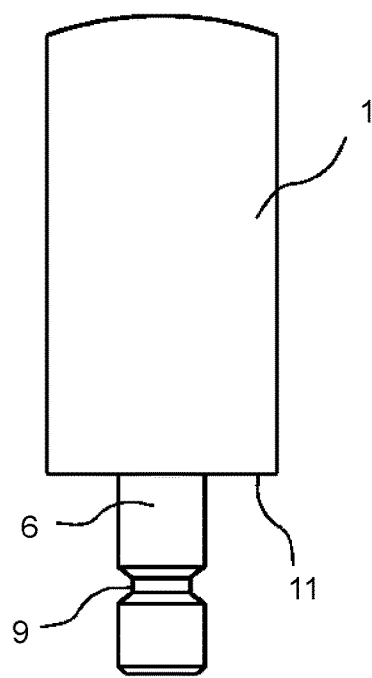
FIG. 2C shows an enlargement of part of the embodiment shown in FIG. 2B.

FIG. 2A shows a first side view of the first panel 1 and FIG. 2B shows a second side view of the first panel 1. FIG. 2C shows an enlargement of the encircled area indicated in FIG. 2B. An embodiment of the rod-shaped element 6 is shown which comprises an embodiment of the tongue groove 9. The rod-shaped element 6 has a longitudinal shape with a length direction which is parallel to the first panel surface. A first crosscut of the rod-shaped element 6, below and/or above the tongue groove 9, in a plane parallel to the second panel surface 22 may have a circular shape, a rectangular shape, a star shape, an oval shape or a hexagon shape.

A locking of the first panel 1 to the second panel 2 in a second direction which is perpendicular to the first panel surface 12 may be obtained by cooperating locking surfaces between the first element groove 7 and the rod-shaped element 6.

A locking of the first panel 1 to the second panel 2 in a third direction which is perpendicular to the first direction and the second direction surface may be obtained by cooperating locking surfaces between the first element groove 7 and the rod-shaped element 6.

A second crosscut of the first element groove 7, in a plane parallel to the second panel surface 22, preferably has a shape that matches a first crosscut of the rod-shaped element 6, in a plane parallel to the second panel surface 22. An advantage of this may be that an improved locking of the first panel 1 to the second panel 2 in the second direction is obtained and/or an improved locking of the first panel 1 to the second panel 2 in a third direction is obtained.

Figure 3:
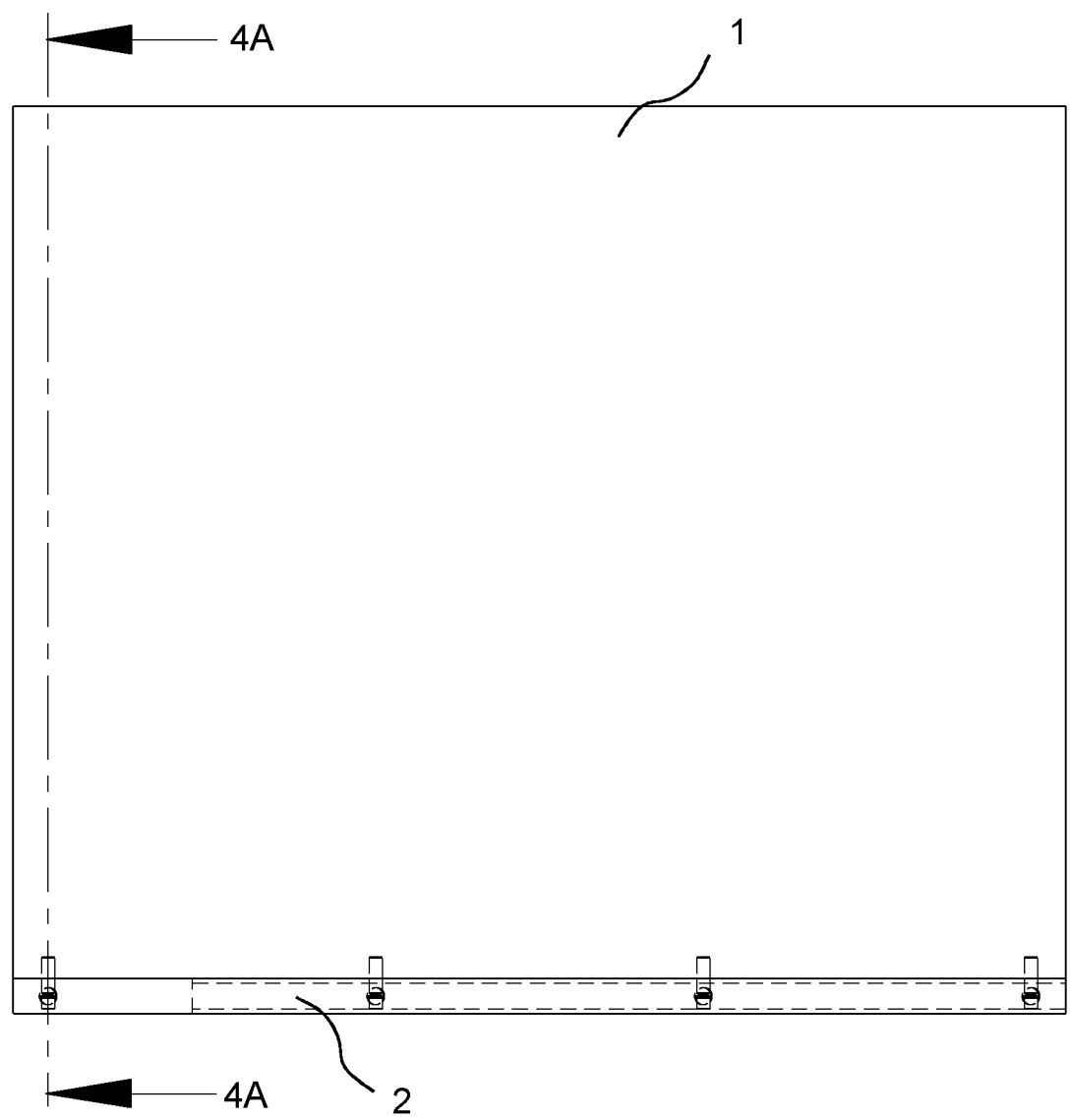
FIG. 3 shows an embodiment of the first panel and the second panel in a locked position according to an embodiment of the invention.

FIG. 3 shows a side view of the first panel 1 and the second panel 2, for a furniture, in a locked position.

FIG. 8A shows a crosscut of an embodiment of the first panel 1 and the second panel 2, for a floor product, in a locked position.

Figure 5A:
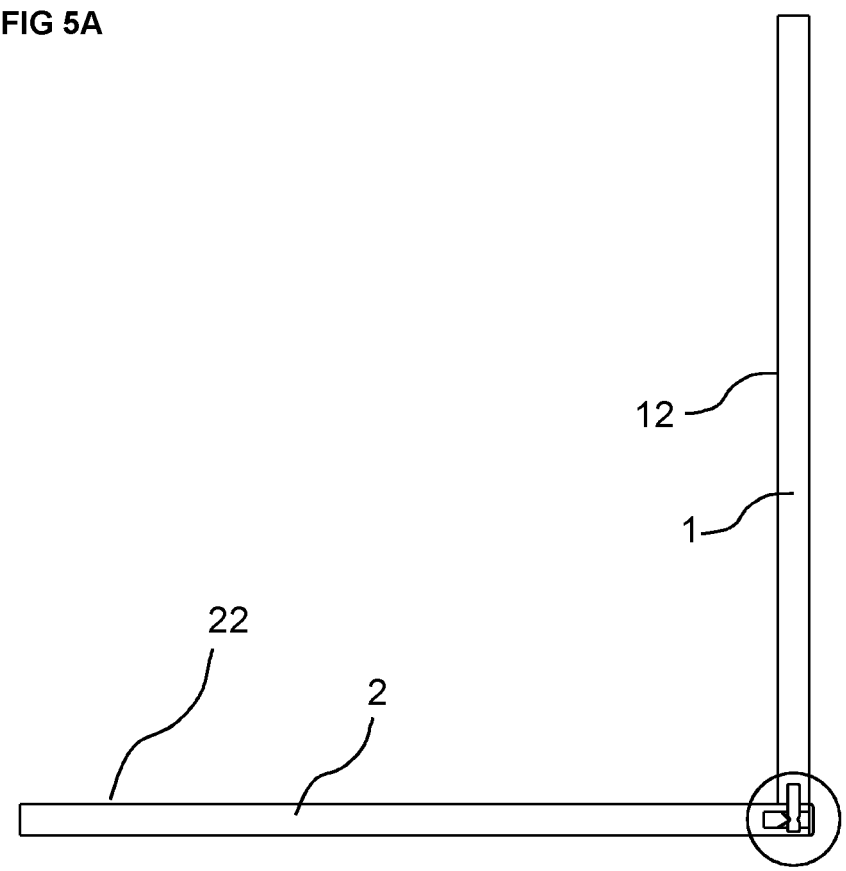
FIG. 5A shows a cross section of an embodiment of the first panel and the second panel in a locked position according to an embodiment of the invention.
Figure 5B:
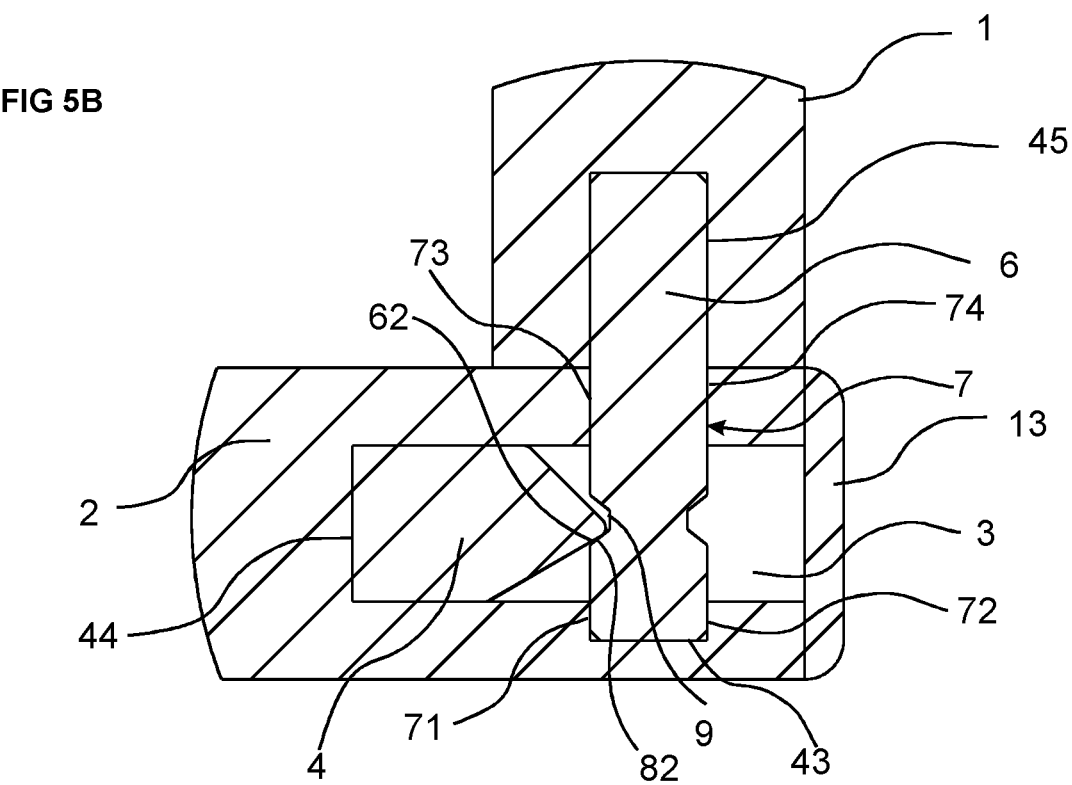
FIG. 5B shows an enlargement of a part of the embodiment shown in FIG. 5A.
Figure 6A:
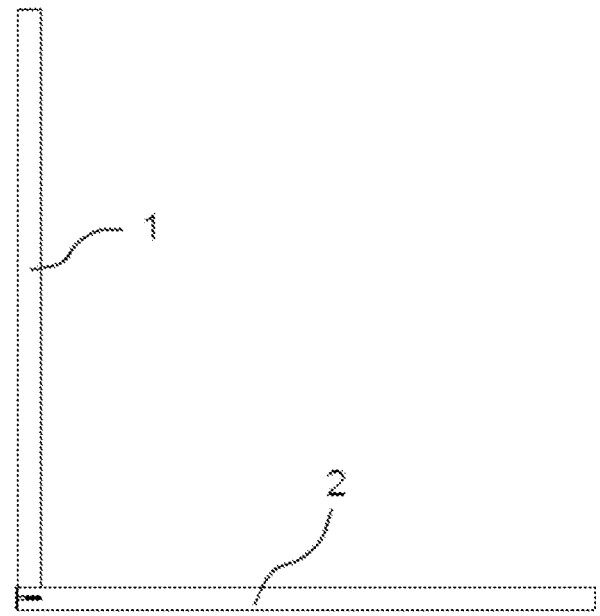
FIGS. 6A-6B show side views of an embodiment of the first panel and the second panel in a locked position according to an embodiment of the invention.
Figure 6B:
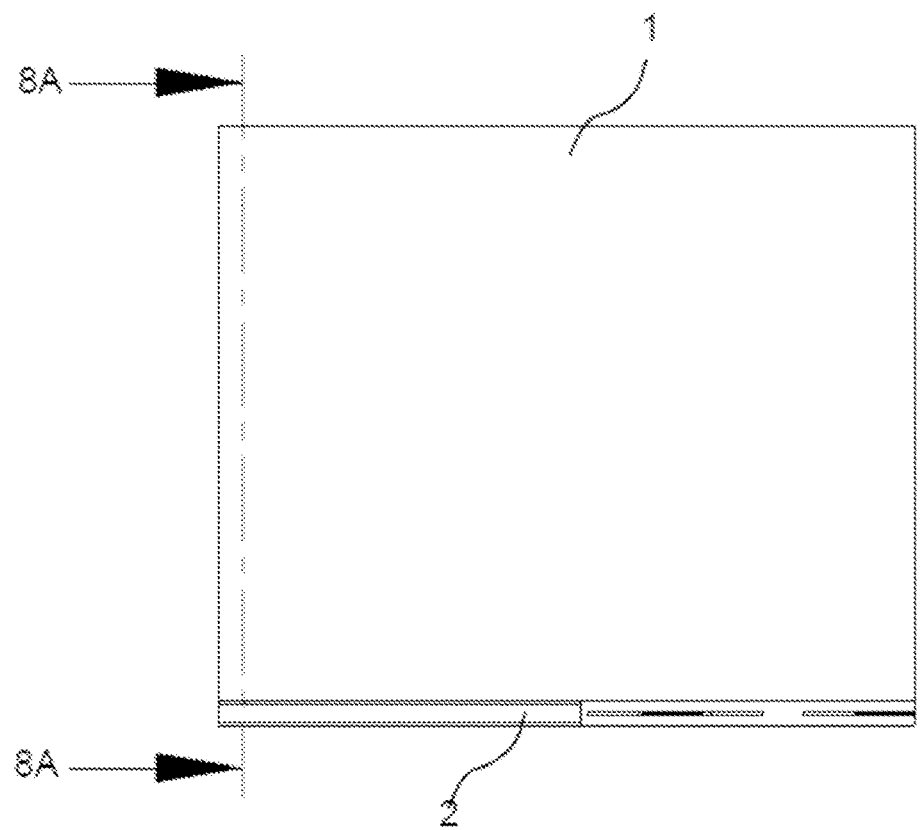
Figure 7A:
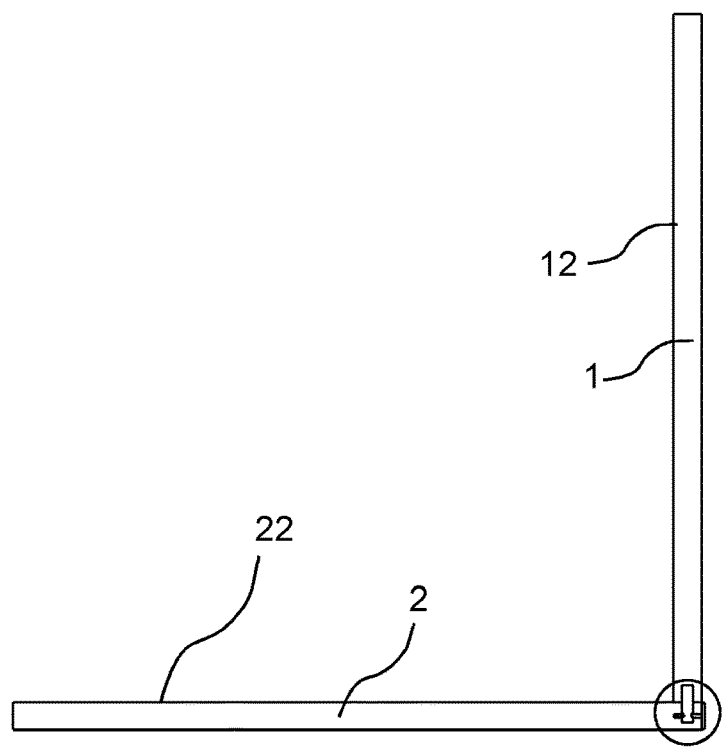
FIG. 7A shows a cross section of an embodiment of the first panel and the second panel in a locked position according to an embodiment of the invention.
Figure 7B:
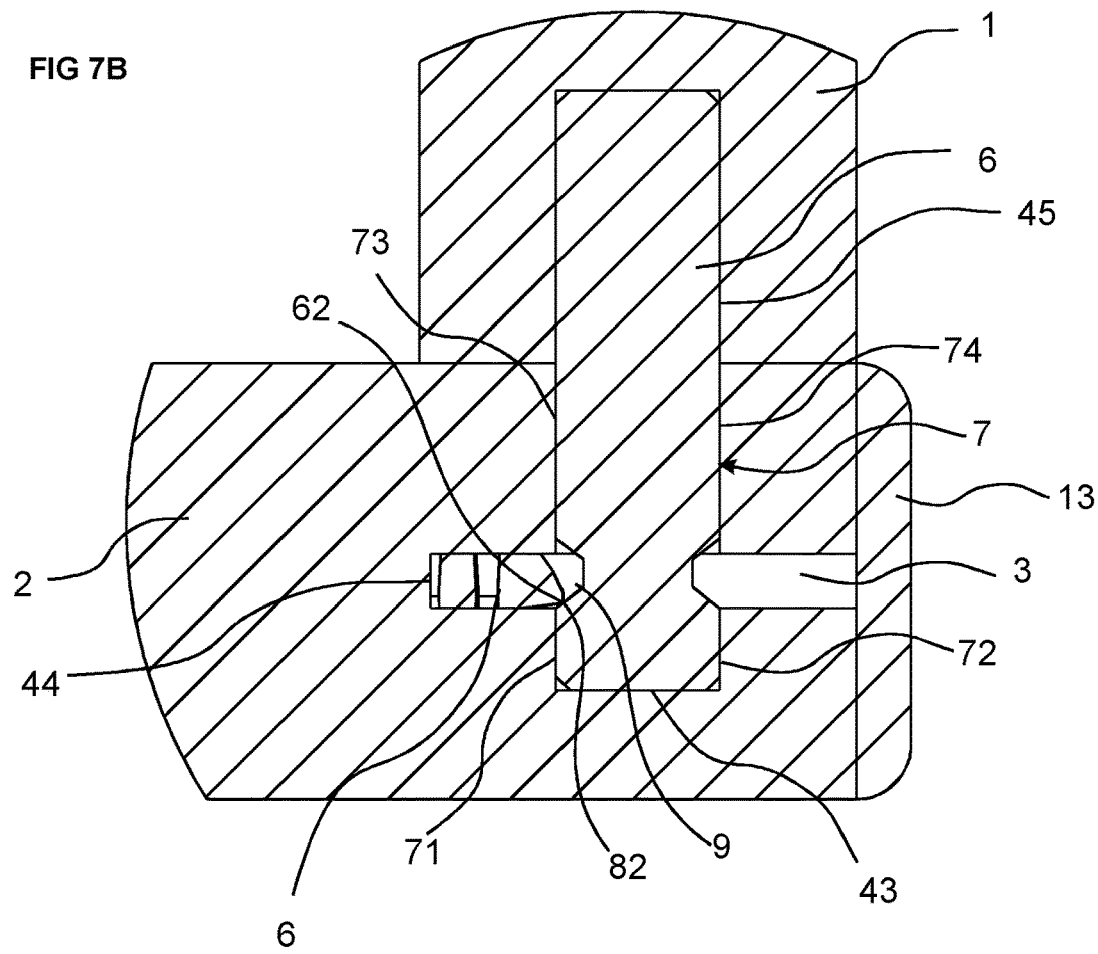
FIG. 7B shows an enlargement of a part of the embodiment shown in FIG. 7A.

FIG. 5A shows a crosscut, at the line indicated by 4A in FIG. 3; of the first panel 1 and the second panel 2 in the locked position. FIG. 5B shows an enlargement of the encircled area indicated in FIG. 5A. The first element groove 7 may extend from the second panel surface 22 to the insertion groove 3. A locking surface 62 of the flexible tongue 4 may cooperate with a locking surface 82 of tongue groove 9 for the locking of the first panel to the second.

The first element groove 7 may comprise a bottom-ended groove, such as a bottom ended drill hole, comprising a bottom surface 43 which is positioned at a distance from the insertion groove 3.

The first element groove 7 may have a first part on a first side of the insertion groove 3 and a second part on a second side of the insertion groove 3, wherein the second part comprises a bottom surface 43 and side walls 71, 72, wherein, in a locked position, the rod-shaped element 6 passes through the first part of the first element groove 7, through the insertion groove 3 and into the second part of the first element groove 7.

The rod-shaped element 6 may be configured to cooperate, for the locking in the second direction, with the side walls 71, 72 of the second part of the first element groove 7.

The rod-shaped element 6 may be configured to cooperate, in a locked position, with the bottom surface 43, or may be configured not to cooperate, in a locked position, with the bottom surface, i.e., leaving a gap between the rod-shaped element 6 and the bottom surface 43.

The first part may comprise side walls 73, 74, wherein the rod-shaped element 6 may be configured to cooperate, for the locking in the second direction, with side walls 73, 74 of the first part.

The sidewalls may comprise material of the core of the second panel 2.

The insertion groove 3 may extend from the second edge surface 21 to the first element groove 7.

The insertion groove 3 may be a bottom-ended groove, comprising a bottom surface 44 which is positioned at a distance from the first element groove 7.

The flexible tongue 4 may be arranged at the bottom surface 44 of the insertion groove 3.

The flexible tongue 4 may be arranged between the tongue groove 9 and the bottom surface 44 of the insertion groove 3 in the locked position.

The rod-shaped element 6 may be configured to be attached in an attachment groove 45 in the first edge surface 11.

The rod-shaped element 6 may be configured to be glued in the attachment groove 45 in the first edge surface 11.

The rod-shaped element 6 may be configured to be locked in the attachment groove 45 by a friction connection or by a mechanical connection, such as threads or by a locking element, such as a barb.

The second edge surface 21 may be essentially perpendicular to the second panel surface 22.

An embodiment of the invention is shown in FIGS. 4A-B, 6A-7B and 9A-10, including a set comprising a first panel 1, a second panel 2 and a mechanical locking device for locking the first panel 1 to the second panel 2. The embodiment comprises an embodiment of the insertion groove 3 which is a longitudinal groove that extends in a longitudinal direction of the second edge surface 21. A locking surface 62 of the flexible tongue 4 may cooperate with a locking surface 82 of tongue groove 9 for the locking of the first panel to the second.

Figure 9C:
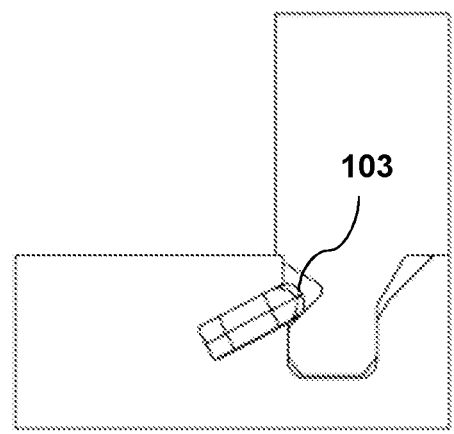
FIGS. 9C-9D show cross section of the first and second panel in a locked position and during assembling.

FIG. 9C shows an embodiment of the invention, where a first panel 1 is locked to a second panel 2. The flexible tongue 4 is inserted in the insertion groove 3 of the second panel 2, and the tongue groove 9 of the first panel cooperates with the first 101 or second 102 locking surface of the tongue 4 for locking of the first panel 1 to the second panel 2.

Figure 9D:
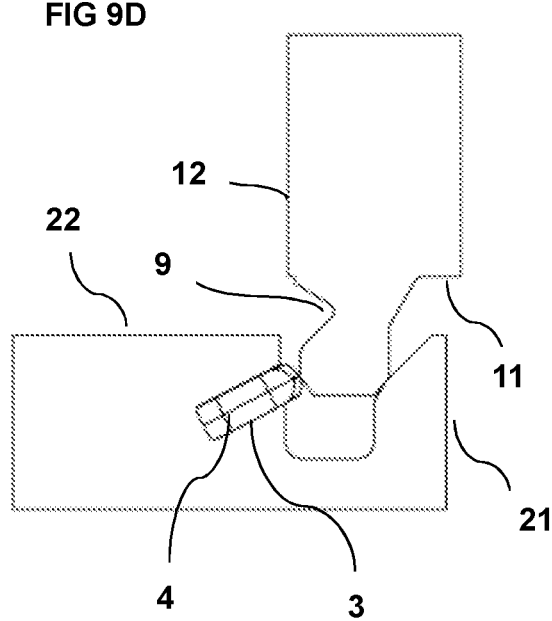
Figure 10:
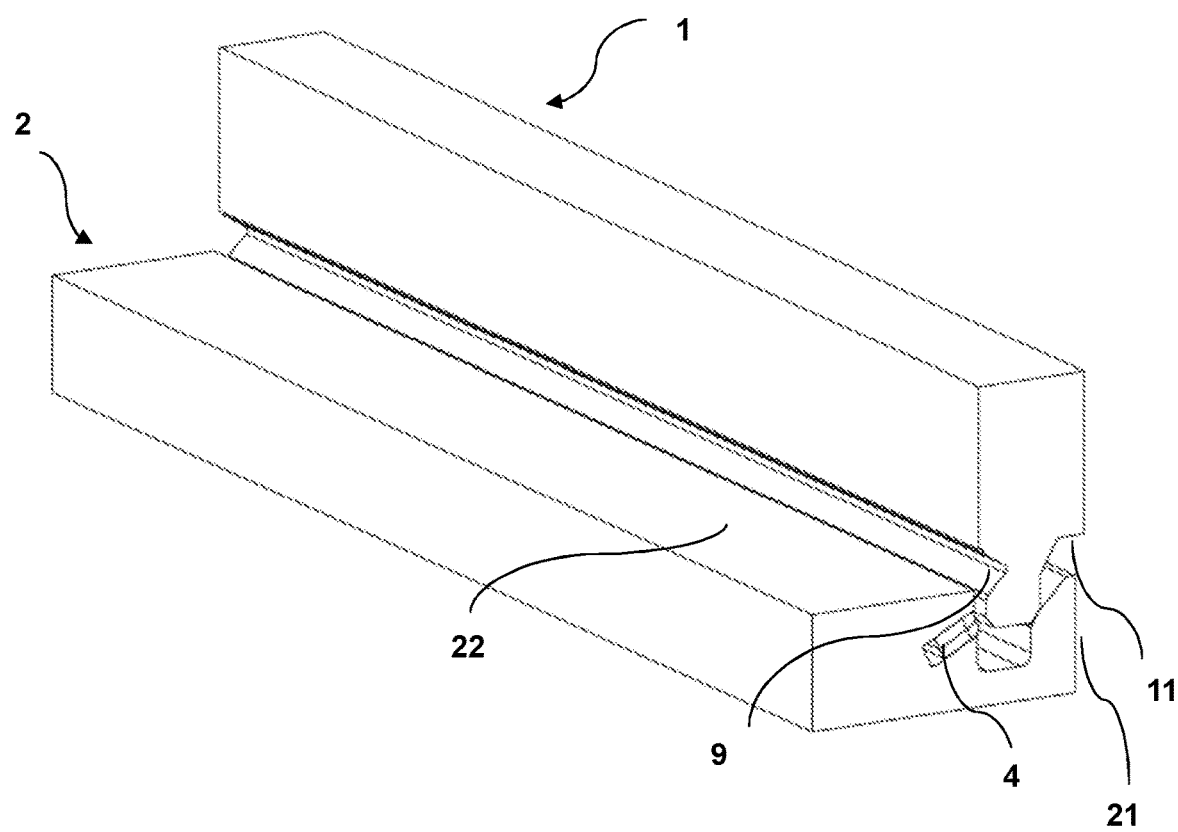
FIG. 10 shows a 3D-view of the first and second panel during assembling.

FIGS. 9D and 10 show an embodiment during assembling, where the embodiment as illustrated in 3D in FIG. 10 shows the locking device of first panel 1 made in one whole piece together with the panel 1, and that the tongue 4 is inserted in the insertion groove 3 of the second panel 2. This is an alternative to using the rod-shaped elements 6.

FIG. 4A shows an embodiment in a 3D view during assembling. The first panel may be assembled by displacing the first panel relative the second panel 2 in a direction which is perpendicular to the second panel surface 22. The mechanical locking device may be configured to automatically lock the first panel 1 to the second panel 2 when the rod-shaped element 6 is inserted into the first element groove 7 and the first edge surface 11 is arranged against second panel surface 22.

The first element groove 7 may be formed in the second panel surface 22 and in a core of the second panel 2.

The second panel surface 22 may comprise a decorative layer and the first element groove 7 may extend though the decorative layer.

The first element groove 7 may be formed by mechanical cutting, such as milling or sawing.

An edge element 13, such as an edge band, is preferably attached to the second edge surface 21 for covering the insertion groove 3 and for enforcing the second edge surface 21. The edge element 13 may be glued to the second edge or attached by a mechanical locking device, which may comprise a part that protrudes from the edge element 13 and is configured to be inserted into the insertion groove 3. The part may be attached to the insertion groove 3 by friction. The edge element 13 is in FIG. 4A partly removed in order to visualize the flexible tongue 4 and the insertion groove 3. The flexible tongue 4 is shown before it is positioned in the insertion groove 3.

Figure 8B:
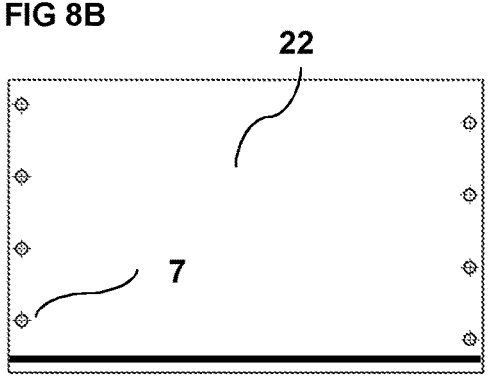
FIGS. 8B-8C show an embodiment of the second panel according to an embodiment of the invention.
Figure 8C:
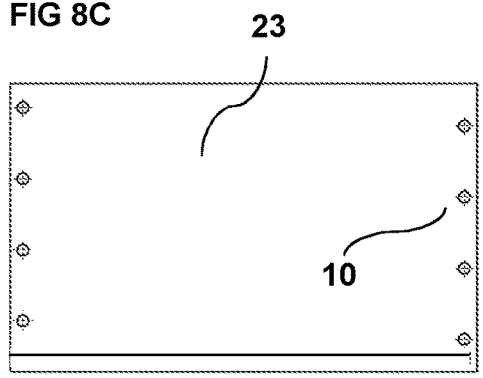
Figure 8D:
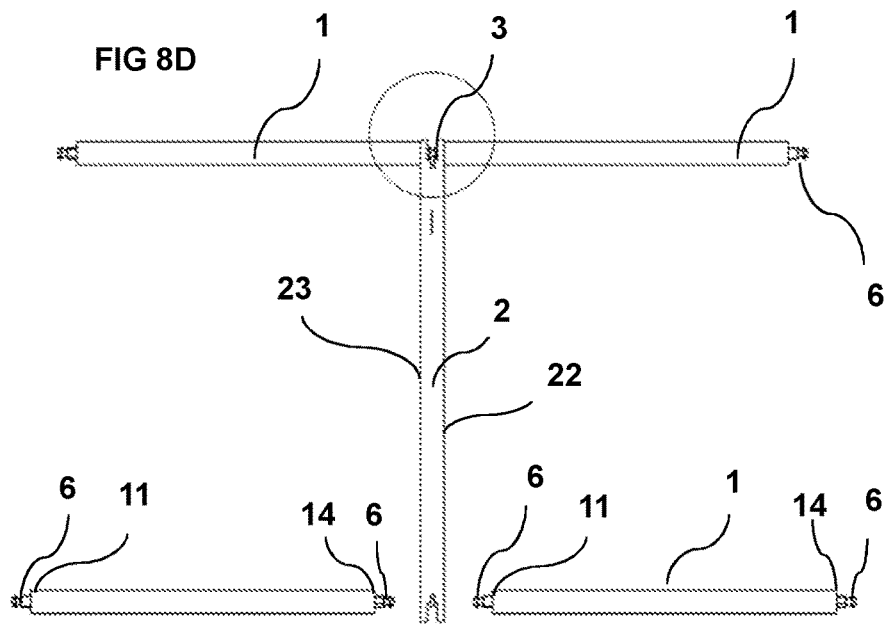
FIG. 8D shows a cross section of an embodiment of the first panel and the second panel during assembling and in a locked position according to an embodiment of the invention.

In a second embodiment of the present invention, e.g., as shown in FIGS. 8B-8D, the edge tongue may be a rod-shaped element 6 at the first edge surface 11 and/or at a third edge surface 14, respectively, of the first panel 1 and the mechanical locking device may comprise a first element groove 7 at the second panel surface 22 and a second element groove 10 at a third panel surface 23 of the second panel 2. The rod-shaped element 6 may comprise the tongue groove 9 and may be configured to be inserted into the first 7 or second 10 element groove. The first element groove 7 may extend from the second panel surface 22 to the insertion groove 3 and the second element groove 10 may extend from the third panel surface 23 to the insertion groove 3. The first locking surface 101 of the flexible tongue 4 may be configured to cooperate with the tongue groove 9 for a locking of the first panel 1 to the second panel 2 in a first direction which is perpendicular to the first panel surface 22 when it is inserted into the first element groove 7 and the first edge surface 11 is arranged against the first panel surface 22. The second locking surface 102 of the flexible tongue 4 may be configured to cooperate with the tongue groove 9 for locking of the first panel 1 to the second panel 2 in a first direction which is perpendicular to the third panel surface 23 when it is inserted into the second element groove 10 and the third edge surface 14 is arranged against the third panel surface 23.

This allows for locking of several panels together, not just as one module, but several modules connected to each other, such as several cubes or rectangular.

As is illustrated in FIGS. 8B-8C, the position of the first 7 and second 10 element groove is displaced horizontally in relation to each other, and correspondingly the position of the rod-shaped element 6 at the first 11 and third 14 edge surface is displaced in relation to each other to fit in to the first 7 and second 10 element groove.

FIG. 8D shows an embodiment which includes a second panel 2 comprising an embodiment of the insertion groove 3 (the encircled area in the drawing) with a flexible tongue 4. The flexible tongue 4 locks the first panel 1 to the second panel surface 22 of the second panel 2 and another of said first panel 1 to the third panel surface 23 of the second panel 2. The first locking surface 101 of the flexible tongue 4 cooperates with the tongue groove 9 of the rod-shaped element 6 at the first edge surface 11 of the first panel 1 and the second locking surface 102 of the flexible tongue 4 cooperates with the tongue groove 9 of the rod-shaped element 6 at the third edge surface 14 of said another first panel 1. Thus, one flexible tongue 4 may cooperate with two rod-shaped elements 6, one from each side of the tongue. In other embodiments, each tongue only cooperates with a single rod-shaped element 6.

The first panel 1 and the rod-shaped element 6 of the second embodiment may be identical to the first panel 1 and the rod-shaped element 6, respectively, of the first embodiment.

The features and characteristics as described above for the first element groove 7 also apply to the second element groove 10.

A first crosscut of the rod-shaped element 6, in a plane parallel to the first 22 or second 23 panel surface may have a circular shape or a rectangular shape.

The mechanical locking device may be configured to automatically lock the first panel 1 to the second panel 2 when the rod-shaped element 6 is inserted into the first 7 or second 10 element groove and the first edge surface 11 is arranged against the first panel surface 22 and/or the third edge surface 14 is arranged against the second 23 panel surface.

The rod-shaped element 6 may have a longitudinal shape with a length direction which is parallel to the first panel surface 12 of the first panel 1.

The insertion groove 3 may extend from the second edge surface 21 to the first element groove 7.

The insertion groove 3 may extend from the second edge surface to the second element groove 10.

The insertion groove 3 may comprise a first surface, an opposite second surface and a bottom surface 44 extending between the first surface and the opposite second surface.

The bottom surface 44 may be positioned at a distance from the first 7 and/or second 10 element groove.

The bendable part 61 of the flexible tongue 4 may be arranged at the bottom surface 44 of the insertion groove 3.

The flexible tongue 4 may be arranged at the bottom surface 44 of the insertion groove 3.

The flexible tongue 4 may be arranged between the tongue groove 9 and the bottom surface 44 of the insertion groove 3 in the locked position.

The support surface 104 and a side surface 105 of the flexible tongue 4 preferably have edges that are rounded to reduce the risk of fibers falling off from the insertion groove 3 when the flexible tongue 4 is inserted and moved in the insertion groove 3.

A part of the flexible tongue 4 may be configured to be displaced against a surface of the insertion groove 3, such as the first surface and/or the second surface.

The core of the first panel 1 and/or of the second panel 2 may be a wood-based core, preferably made of MDF, HDF, OSB, WPC, plywood, or particleboard. The core may also be a plastic core comprising thermosetting plastic or thermoplastic e.g., vinyl, PVC, PU or PET. The plastic core may comprise fillers.

The first panel 1 and/or the second panel 2 may also be of solid wood.

The first panel 1 and/or the second panel 2 may be provided with a decorative layer, such as a foil or a veneer, on one or more surfaces.

The flexible tongue 4 according to the present invention enables a locking on both sides of the flexible tongue due to the first 101 and second 102 locking surface. Since the flexible tongue has locking surfaces on both sides, and thus may be symmetric, there risk of the tongue 4 being inserted in the insertion groove 3 in an incorrect way is strongly reduced.

Further, since the edges of the flexible tongue 4 are rounded, the risk of the flexible tongue 4 being stuck in the insertion groove 3 during the insertion of the flexible tongue 4 is reduced.

Further, the flexible tongue 4, according to an embodiment of the present invention, enables the use of an essentially circular disassembling tool for disassembling of the panels. Such essentially circular disassembling tools are easier to manufacture with a high precision than rectangular disassembling tools. The circular disassembling tools further have a smaller cross-section than the rectangular ones, which has the advantage that a smaller opening in the panel for the disassembling tool is necessary, resulting in a more stable and aesthetic construction when the panels are mounted.

Embodiments

1. A set comprising a first panel (1), a second panel (2) and a mechanical locking device for locking the first panel (1) to the second panel (2), wherein the first panel (1) comprises a first edge surface (11) and a first panel surface (12) and the second panel (2) comprises a second edge surface (21) and a second panel surface (22), characterized in
   that the mechanical locking device comprises an insertion groove (3) at the second edge surface (21), a flexible tongue (4) positioned in the insertion groove (3) and an edge tongue comprising a tongue groove (9),
   that the flexible tongue (4) comprises a first locking surface (101) and a second locking surface (102),
   that the first locking surface (101) is configured to cooperate with the tongue groove (9) for locking of the first panel (1) to the second panel (2) in a first direction when the flexible tongue (4) is positioned in the insertion groove (3) in a first orientation, and
   that the second locking surface (102) of the flexible tongue (4) is configured to cooperate with the tongue groove (9) for a locking of the first panel (1) to the second panel (2) in the first direction when the flexible tongue (4) is positioned in the insertion groove (3) in a second orientation.

2. The set as in embodiment 1, wherein the first locking surface (101) and the second locking surface (102) is essentially symmetrically positioned on the flexible tongue (4).

3. The set as in embodiment 1 or 2, wherein an angle (50) between the first (101) and second (102) locking surface is within the range of about 90° to about 180°, preferably within the range of about 150° to about 175°, or preferably about 158°.

4. The set as in any one of the previous embodiments, wherein the flexible tongue (4) comprises a guiding surface (103) configured to cooperate with the edge tongue during a displacement of the first panel (1) relative to the second panel (2).

5. The set as in embodiment 4, wherein the guiding surface (103) in a first end is connected to the first locking surface (101) and in a second end is connected to the second locking surface (102).

6. The set as in embodiment 4 or 5, wherein the guiding surface (103) has a curved shape.

7. The set as in embodiment 6, wherein the guiding surface (103) has the shape of a circular segment.

8. The set as in embodiment 6 or 7, wherein the curved shape of the guiding surface (103) has a radius between the first (101) and second (102) locking surfaces within the range of about 0.5 mm to about 3 mm, preferably within the range of 1 mm to 2 mm, or preferably about 1.5 mm.

9. The set as in any of embodiments 6 to 8, wherein the flexible tongue has a thickness T and wherein the curved shape of the guiding surface (103) has a radius between the first (101) and second (102) locking surfaces within the range of about 0.2×T to 1.2×T or about 0.4×T to about 0.8×T, or 0.6×T.

10. The set as in any of embodiments 4 to 9, wherein the guiding surface (103) is configured to cooperate with a curved shape surface of a disassembling tool, wherein the disassembling tool preferably has a circular cross section.

11. The set as in any of the previous embodiments, wherein the flexible tongue (4) has a support surface (104) positioned opposite to the guiding surface (103), wherein the support surface (104) has a curved shape with a radius within the range of about 25 mm to about 50 mm, preferably within the range of 30 mm to 45 mm, or preferably about 37 mm.

12. The set as in any of embodiments 6 to 12, wherein the curved shape of the support surface (104) has a radius that is smaller than a radius of a bottom surface (44) of the insertion groove (3).

13. The set as in any of the previous embodiments, wherein the first or second direction for locking of the first panel (1) to the second panel (2) is parallel and/or perpendicular to the second panel surface (22).

14. The set as in any of the previous embodiments, wherein the edge tongue is a rod-shaped element (6) at the first edge surface (11) and at a third edge surface (14) of the first panel (1) and the mechanical locking device comprises a first element groove (7) at the second panel surface (22) and a second element groove (10) at a third panel surface (23) of the second panel (2), wherein the rod-shaped element (6) comprises the tongue groove (9) and is configured to be inserted into the first (7) or second (10) element groove, wherein
the first element groove (7) extends from the second panel surface (22) to the insertion groove (3) and the second element groove (10) extends from the third panel surface (23) to the insertion groove (3),
the first locking surface (101) of the flexible tongue (4) is configured to cooperate with the tongue groove (9) for a locking of the first panel (1) to the second panel (2) in a first direction which is perpendicular to the first panel surface (22) when it is inserted into the first element groove (7) and the first edge surface (11) is arranged against the first panel surface (22); and
the second locking surface (102) of the flexible tongue (4) is configured to cooperate with the tongue groove (9) for locking of the first panel (1) to the second panel (2) in a first direction which is perpendicular to the first panel surface (22) when it is inserted into the second element groove (10) and the third edge surface (14) is arranged against the third panel surface (23).

15. The set as in embodiment 14, wherein a first crosscut of the rod-shaped element (6), in a plane parallel to the first (22) or second (23) panel surface has a circular shape or a rectangular shape.

16. The set as in any of embodiments 14 to 15, wherein the mechanical locking device is configured to automatically lock the first panel (1) to the second panel (2) when the rod-shaped element (6) is inserted into the first (7) or second (10) element groove and the first edge surface (11) is arranged against the first panel surface (22) and/or the third edge surface (14) is arranged against the second (23) panel surface.

17. The set as in any of embodiments 14 to 16, wherein the rod-shaped element (6) has a longitudinal shape with a length direction which is parallel to the first panel surface (12) of the first panel (1).

The invention claimed is:
1. A set for a furniture product comprising a first panel, a second panel and a mechanical locking device for locking the first panel to the second panel, wherein the first panel comprises a first edge surface and a first panel surface and the second panel comprises a second edge surface and a second panel surface, wherein the first panel surface is perpendicular to the second panel surface in a locked position of the first panel and the second panel, wherein:
the mechanical locking device comprises an insertion groove at the second edge surface, a flexible tongue positioned in the insertion groove and an edge tongue at the first edge surface comprising a tongue groove,
the flexible tongue comprises a first locking surface and a second locking surface,
the first locking surface is configured to cooperate with the tongue groove for locking of the first panel to the second panel in a first direction when the flexible tongue is positioned in the insertion groove in a first orientation,
the second locking surface of the flexible tongue is configured to cooperate with the tongue groove for a locking of the first panel to the second panel in the first direction when the flexible tongue is positioned in the insertion groove in a second orientation,
the first locking surface and the second locking surface are positioned on the flexible tongue on both sides of the flexible tongue,
the flexible tongue comprises a guiding surface positioned between the first and second locking surfaces,
the first locking surface and the second locking surface are converging towards each other, and
the guiding surface is configured to cooperate with the edge tongue during a displacement of the first panel relative to the second panel.

2. The set as claimed in claim 1, wherein the first locking surface and the second locking surface are flat, spaced from one another, and symmetrically positioned on the flexible tongue.

3. The set as claimed in claim 1, wherein the first locking surface and the second locking surface are converging towards the guiding surface.

4. The set as claimed in claim 1, wherein a core of the first panel and/or of the second panel is/are a wood-based core.

5. The set as claimed in claim 1, wherein the guiding surface in a first end is connected to the first locking surface and in a second end is connected to the second locking surface.

6. The set as claimed in claim 1, wherein the guiding surface has a curved shape.

7. The set as claimed in claim 1, wherein the guiding surface has a shape of a circular segment.

8. The set as claimed in claim 6, wherein the curved shape of the guiding surface has a radius between the first and second locking surfaces within the range of about 0.5 mm to about 3 mm.

9. The set as claimed in claim 6, wherein the flexible tongue has a thickness T and wherein the curved shape of the guiding surface has a radius between the first and second locking surfaces within a range of about $0.2 \times T$ to $1.2 \times T$.

10. The set as claimed in claim 1, wherein the guiding surface is configured to cooperate with a curved shape surface of a disassembling tool.

11. The set as claimed in claim 1, wherein the flexible tongue has a support surface positioned opposite to the guiding surface, wherein the support surface has a curved shape with a radius within the range of about 25 mm to about 50 mm.

12. The set as claimed in claim 6, wherein the curved shape of the support surface has a radius that is smaller than a radius of a bottom surface of the insertion groove.

13. The set as claimed in claim 1, wherein the first direction or a second direction for locking of the first panel to the second panel is parallel and/or perpendicular to the second panel surface.

14. The set as claimed in claim 4, wherein the wood-based core comprises a MDF, HDF, OSB, plywood or particleboard.

15. The set as claimed in claim 4, wherein the wood-based core is of solid wood.

* * * * *